United States Patent
Ogiso et al.

(10) Patent No.: US 6,627,288 B1
(45) Date of Patent: Sep. 30, 2003

(54) OPTICAL RECORDING MEDIUM AND PORPHYCENE COMPOUND

(75) Inventors: Akira Ogiso, Chiba (JP); Shinobu Inoue, Chiba (JP); Hisashi Tsukahara, Chiba (JP); Taizo Nishimoto, Chiba (JP); Tsutami Misawa, Chiba (JP); Tadashi Koike, Chiba (JP)

(73) Assignees: Mitsui Chemicals, Inc., Tokyo (JP); Yamamoto Chemicals, Inc., Osaka (JP)

( * ) Notice: Subject to any disclaimer, the term of this patent is extended or adjusted under 35 U.S.C. 154(b) by 64 days.

(21) Appl. No.: 09/919,890

(22) Filed: Aug. 2, 2001

(30) Foreign Application Priority Data

Aug. 10, 2000 (JP) ........................................ 2000-242608

(51) Int. Cl.[7] ................................................. B32B 3/02
(52) U.S. Cl. ................. 428/64.1; 428/64.8; 430/270.14
(58) Field of Search ............................... 428/64.1, 64.4, 428/64.8, 913; 430/270.14, 495.1, 945; 369/283, 288

(56) References Cited

U.S. PATENT DOCUMENTS

| | | | | |
|---|---|---|---|---|
| 5,179,120 A | * | 1/1993 | Vogel | 514/410 |
| 5,486,437 A | * | 1/1996 | Iwamura | 369/288 |
| 5,610,175 A | | 3/1997 | Vogel et al. | |
| 5,616,342 A | | 4/1997 | Lyons | |
| 6,008,211 A | * | 12/1999 | Robinson | |
| 6,454,951 B1 | | 9/2002 | Jori | |

FOREIGN PATENT DOCUMENTS

| | | |
|---|---|---|
| JP | 6-508834 | 10/1994 |
| JP | 11-502520 | 3/1999 |
| JP | 11-503159 | 3/1999 |
| JP | 2000-505439 | 5/2000 |
| JP | 2001 039032 A | 2/2001 |
| JP | 2001-84594 A | 3/2001 |
| JP | 2001 100353 A | 4/2001 |
| JP | 2001-180117 A | 7/2001 |
| JP | 2001-338768 A | 12/2001 |
| JP | 2002-114923 A | 4/2002 |
| JP | 2002-123938 A | 4/2002 |
| JP | 2002-237385 A | 8/2002 |
| JP | 2002-337452 A | 11/2002 |
| WO | 97 29636 A | 8/1997 |

OTHER PUBLICATIONS

Richert, C., et al., "Photodynamic Antitumor Agents: Beta-Methoxyethyl Groups Give Access to Functionalized Porphycenes and Enhance Cellular Uptake and Activity." Journal of Medicinal Chemistry. American Chemical Society, Washington, DC. vol. 37, 1994, pp. 2797–2807.

Nonell, S. et al. Synthesis of 2, 7, 12, 17-Tetraphenylporphycene (TPPo). "First Aryl–Substituted Porphycene for the Photodynamic Therapy of Tumors." Tetrahedron Letters. Elsevier Science Publishers, Amsterdam, NL. vol. 36, No. 19, May 8, 1995, pp–3405–3408.

Sepiol et al., "Proton tunnelling in porphycene seeded in a supersonic jet.", Chemical Physics Letters, 1998, pp. 549–556, 296, Elsevier Science B.V.

Altmann et al., "Dipole moment differences of nonpolar dyes in polymeric matrices: Stark effect and photochemical hole burning," J. Chemical Physics, Oct. 15, 1992, pp. 5316–5322, vol. 97, No. 8, American Institute of Physics.

Kadish et al., "Electrochemistry of New σ–Bonded Metal(III) Complexes with Tetrapyrrole Ligands," Inorganic Chemistry, 1994, pp. 4474–4479, vol. 33, No. 20, American Chemical Society.

* cited by examiner

*Primary Examiner*—Elizabeth Mulvaney
(74) *Attorney, Agent, or Firm*—Burns, Doane, Swecker & Mathis, LLP

(57) ABSTRACT

A recordable optical recording medium of this invention capable of good recording and reproduction with a laser at wavelengths of 300 to 500 nm and/or 500 to 700 nm comprises at least one porphycene compounds optionally chelated with a metal in its recording layer.

33 Claims, 3 Drawing Sheets

OPTICAL RECORDING MEDIUM AND PORPHYCENE COMPOUND

BACKGROUND OF THE INVENTION

1. Field of the Invention

This invention relates to a porphycene compound useful as a dye, a pigment, a photoelectric functional material and a recording or storage material, in particular as a recording dyestuff for a large recordable optical recording medium whereby information can be recorded and/or reproduced using a blue and/or red laser beam. This invention also relates to an optical recording medium comprising the porphycene compound.

This invention also relates to an optical information recording medium comprising a recording layer capable of high-density recording where recording is particularly conducted using a blue-violet laser with a wavelength of 400 to 410 nm.

2. Description of the Related Art

It is well known that a CD-R (CD-Recordable) has been proposed and developed as a recordable optical recording medium complying to Compact Disk (hereinafter, referred to as CD) specifications and that it has been wide spread for music reproduction and an information terminal.

Generally, a near infrared semiconductor laser at 770 nm to 830 nm is used for recording and/or reproduction of the optical recording medium, where a signal is recorded on a recording layer made of, for example, an organic dye on a substrate in a heat mode. Specifically, when the recording layer is irradiated with a laser beam, optical absorption occurs so that the organic dye generates heat, by which a pit is formed in the recording layer. A recording signal can be detected from difference in a reflectance between areas with and without the pit during laser-beam irradiation.

Such a medium is compliant with CD specifications such as Red Book and Orange Book and is, therefore, characterized in that it may be interchangeably used in a CD and a CD-ROM players. The existing medium, however, has a recording capacity of about 680 MB, which is not adequate in the light of recording of a moving picture. Thus, there has been the need for a higher density and a larger capacity in an information recording medium as a quantity of information has been dramatically increased.

A higher density of a recording medium may be achieved by reducing a wavelength of a laser beam used in recording and reproduction and increasing a numerical aperture (N.A.) in an objective lens. There has been practically used a short wavelength laser at, e.g., 680 nm, 670 nm, 660 nm, 650 nm or 635 nm. Thus, reduction in a wavelength of a semiconductor laser, increase of an N.A. in an objective lens and a data compaction technique have allowed us to obtain an optical recording medium capable of recording a moving picture or a large quantity of information. Consequently, a recordable digital versatile disk (hereinafter, referred to as DVD-R) has been developed as a recordable optical recording medium in response to the above laser beam. A DVD-R is an optical recording medium with a recording capacity of 3.9 GB or 4.7 GB which is writable only once. There has been further the need for developing an optical disk exhibiting good recording properties suitable to the capacity. A red laser used in the medium has a wavelength of 550 nm to 700 nm, preferably about 635 nm to 660 nm. Optical recording media which have been suggested for the conditions include magneto-optical media, phase-change recording media, chalcogen-oxide optical recording media and organic-dye optical recording media. Among these, organic-dye optical recording media might be preferable in the light of their lower cost and good processability.

Recordable optical recording media comprising a recording layer in which a dye is employed and a reflecting layer formed on the recording layer for improving a reflectance have become widely marketed as recordable compact disks (Compact Disk Recordable; CD-R) employing a cyanine or phthalocyanine dye in a recording layer since they have been disclosed in, for example, Optical Data Storage 1989 Technical Digest Series Vol. 1, 45 ('89). These media may permit recording with a semiconductor laser at 780 nm and the data may be reproduced by a widely marketed CD or CD-ROM player equipped with a semiconductor laser device at 780 nm.

Furthermore, DVD-R media with a capacity of 4.7 GB in one side have been recently marketed as an optical recording medium with a higher density than a CD and capable of recording and reproduction of a moving picture with TV quality, in which recording is conducted using a red semiconductor laser with an emission wavelength of 635 to 660 nm and which can be reproduced by a growing commercial DVD video player or DVD-ROM player. Such a DVD-R medium also employs a lamination structure where a dye such as a cyanine and an azo dyes is used in a recording layer and a reflecting layer is formed, having a disk structure where two substrates with a thickness of 0.6 mm are laminated.

It is expected that much higher recording will be in future required, resulting in a larger capacity of 15 to 30 GB. It may be, therefore, inevitable to use a laser with a much shorter wavelength to achieve such a recording density. Therefore, a dye exhibiting good recording properties within a wavelength range of 300 to 500 nm will be required as a recording dye used in a future organic-dye type of optical recording medium.

In terms of a medium which can conduct higher-density recording than a DVD-R using an organic dye as a recording layer, JP-A 10-302310 has disclosed that a laser with an emission wavelength of 680 nm or less may be used to achieve a density corresponding to a recording capacity of 8 GB or more. The publication has suggested that a laser at 680 nm or less may be focused using an objective lens having an N.A. of 0.7 or more through a light transmitting layer with a thickness of 10 to 177 $\mu$m to achieve recording with a large capacity of 8 GB or more.

Meanwhile, there have been, as a blue laser, developed a laser at 410 nm using a GaN material and a SHG laser at 425 nm which is a combination of a semiconductor laser and an optical waveguide device (See e.g., Nikkei Electronics No.708, p.117, Jan. 26 (1998)). There have been attempts for developing a dye for a blue semiconductor laser in response to such a laser.

Since Nichia Corporation distributed samples of a GaN semiconductor laser with blue-violet emission at an emission wavelength of 390 to 430 nm from the beginning of 1999, there has been investigated a medium which has a further higher density capacity of 15 GB or more in one side and can record a moving picture for about 2 hours with an HDTV (high definition television) broadcasting quality (hereinafter, referred to as an "HD-DVD-R medium"). Such an HD-DVD-R medium with a high density capacity allow us to conduct recording for about 6 hours with image quality in current broadcasting. It has been, therefore, paid much attention as a new recording medium in place of a home VTR. A technical review of a medium using an inorganic recording film made of a phase change material has been published in Nikkei Electronics, No. 751, p.117, Sep. 6 (1999).

To date, dyes recordable with a blue laser at 400 nm to 500 nm include cyanine dyes described in JP-As 4-74690 and 6-40161; porphyrin dyes described in JP-As 7-304256, 7-304257, 8-127174 and 11-334207; polyene dyes described in JP-As 4-78576 and 4-89279; azo dyes described in JP-As 11-334204 and 11-334205; dicyanovinylphenyl dyes described in JP-A 11-304206; coumarin compounds described in JP-A 2000-43423; and pyrimidine compounds described in JP-A 2000-163799.

Other examples include an optical recording medium described in JP-A 11-53758 comprising two layers, i.e., a recording layer mainly containing, e.g., a porphyrin dye or cyanine dye as an organic dye for forming a recording layer and a metal reflecting layer mainly containing silver; an optical recording medium described in JP-A 11-203729 with an improved medium configuration which has a blue-laser sensitive dye layer comprising a cyanine dye responding to a blue laser and a red-laser sensitive dye layer to allow us to conduct recording in two wavelength regions; an optical recording medium described in JP-A 11-78239 using an indigoid dye in which two dyes for a blue and a red lasers are mixed to allow us to conduct recording in two wavelength regions; an optical recording medium described in JP-A 11-105423 using a cyanoethene dye; and an optical recording medium described in JP-A 11-110815 using a squalirium dye.

Furthermore, JP-As 7-304256 and 7-304257 have described as an example of recording using an organic dye film in a blue range of 400 to 500 nm that a porphyrin compound is mixed with a molecular compound and a polymer coordinating to a central metal in the porphyrin compound or a polymer having a side chain coordinating to the central metal to make the Soret band in the porphyrin compound shift to a longer wavelength side for an Ar laser at 488 nm while allowing a film to be formed by spin coating. According to our investigation, polyene dyes such as those described in JP-As 4-78576 and 4-89279 have poor light stability and require improvement such as blending of quenchers for practical use.

Optical recording media recordable to both wavelength-region lasers include optical recording media using a porphyrin compound described in JP-A 10-101953 and a tetraazaporphyrin dye described in JP-A 11-144312. Specifically, porphyrin compounds and azaporphyrin dyes having a similar structure exhibit an absorption called as the "Q band" in a longer wavelength side in the visible region and also a strong absorption called as the "Soret band" in a shorter wavelength side in the visible region. The publication has implied that a circular organic compound such as porphyrin widely used in a dye, pigment, photoelectric functional material or so on may be a compound having properties as a dye for a DVD-R as well as an optical recording medium by which higher-density recording can be conducted in response to 15 to 30 GB.

Recently, since practical use of a blue-violet laser with a wavelength of 400 nm to 410 nm has become feasible, large-capacity recordable optical recording media using the laser have been intensely developed, and in particular, there have been the need for developing a dye exhibiting good light resistance and good rapid-recording properties.

The above optical recording medium for a blue semiconductor laser is, however, inadequately suitable to a laser beam at a wavelength of 400 nm to 410 nm. Specifically, we have found, for example, a problem that a medium using the organic dye does not necessarily give a good ratio between a carrier wave and a noise (C/N) for reproduction of a recorded signal, sometimes leading to unsatisfactory signal reading. It has become urgent to develop an optical recording medium capable of recording and reproducing with a higher density using a laser beam at a wavelength of 400 nm to 410 nm by solving the problem. Furthermore, it is essential to incorporate an organic dye responding to a laser wavelength of 635 nm to 660 nm in a recording layer for accommodating a DVD-R with a capacity of 4.7 GB strongly needed as a recording/reproducing medium for a digital moving image. The objective cannot be achieved only by the above recording dye exclusively for a blue laser wavelength.

Furthermore, an optical recording medium described in JP-A 11-203729 capable of recording and reproducing in two wavelength regions, i.e., a blue and a red laser wavelength regions, must have a plurality of recording layers. An optical recording medium described in JP-As 11-78239, 11-105423 and 11-110815 must comprise at least two recording dyes, leading to a complicated preparation process for the medium and there is a room for improvement in recording properties. An optical recording medium described in JP-As 11-101953 and 11-144312 has not been optimized for recording/reproduction using each laser beam selected within both wavelength regions of 400 nm to 410 nm and 635 nm to 660 nm.

We have investigated recording materials suitable to a recordable optical recording medium and have finally found the followings:

(1) Since a large-capacity recordable optical recording medium employs a laser beam at 300 to 500 nm and/or 500 to 700 nm for writing and reading a record, it is important that a recording material is controlled for its absorption coefficient, refractive index and reflectance near a laser wavelength;

(2) There have been intensely developed large-capacity recordable optical recording media using the laser and in particular, there has been the need for developing a dye exhibiting good light resistance and good high-speed recording properties. The above dye as a recording material recordable and reproducible to a laser within these wavelength regions, however, has not exhibit adequate properties and there are a room for improvement. Furthermore, preparation of a medium by an application process such as spin coating in which a recording film may be readily formed has an advantage that it exhibits higher solubility in an applied solvent and thus the advantage must be also considered.

It is generally necessary to conduct higher-density recording for increasing a recording capacity. It is, therefore, essential to increase an N.A. for an objective lens for focusing an optical beam used for recording and to reduce a wavelength of a laser beam in an optical system. A minimum beam diameter in the focused optical beam depends on a diffraction limit.

Meanwhile, since recording is conducted when a beam intensity exceeds a threshold, a recording pit smaller than a focused beam spot is formed as seen in FIG. 6(a). The area surrounding the pit corresponds to the periphery of the intensity peak. As a wavelength becomes shorter, the periphery of the recording pit tends to accelerate a photochemical reaction of the recording layer. Particularly, the above wavelength region of a blue-violet laser becomes a wavelength region where a photochemical reaction of an organic compound easily occurs, leading to problems of deterioration in a pit edge during recording and poor signal properties. Specifically, as shown in FIG. 6(b), recording information which must be ideally formed in response to a rectangular wave (the solid line in FIG. 6(b)) exhibits a broad waveform (the broken line in FIG. 6(b)) due to deterioration in a pit edge. There is also a problem that when using the same blue-violet laser wavelength as that in recording, even a weak irradiation like a reproduction light may accelerate a photo reaction to promote deterioration after each reproduction. JP-As 7-304256 and 7-304257 have taken a measure that a reproduction light has a different from, substantially longer than, a recording light. Thus, the requirement of a higher density cannot be adequately met. The use of a recording and a reproduction lights with different wavelengths means that a recording and a reproduction devices must be separately prepared or one device must have two optical systems and their control systems, which may lead to limitation in applications as an optical recording medium, a larger apparatus, an increased cost and thus poor utility. Furthermore, in a conventional optical recording medium such as a CD-R, ON/OFF of recording has been controlled through an explicit thermal threshold in a physical property such as a melting point, a sublimation point, a phase transition point or a thermal decomposition point of an organic dye film. Involvement of optical deterioration mode due to blue-violet-laser excitation make the contrast obscure. In particular, it may significantly deteriorate recording signal quality in a high-density recording system where a minute recording pit smaller than an optical beam must be formed.

SUMMARY OF THE INVENTION

An objective of this invention is to provide an optical recording medium capable of high-quality optical recording and reproduction by preparing an optimal dye for recording/reproduction of information using a light.

We have intensely attempted for solving the above problems and have finally achieved this invention.

Specifically, this invention provides the followings.

(1) An optical recording medium having a recording layer comprising at least one compound selected from optionally metal-complexed porphycenes.

(2) The optical recording medium having an organic dye layer as a recording layer on a substrate, comprising at least one compound selected from the compounds as defined in the above (1) in the organic dye layer.

(3) The above optical recording medium wherein the compound is represented by general formula (1):

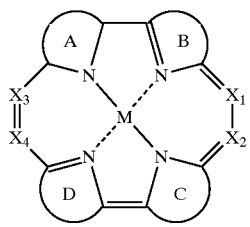

(1)

wherein the rings A, B, C and D independently represent an optionally substituted pyrrole ring; $X^1$, $X^2$, $X^3$ and $X^4$ independently represents optionally substituted methine group; and M represents two hydrogen atoms, a bivalent to tetravalent metal, metalloid or oxymetal atom optionally having a substituent or ligand.

(4) The above optical recording medium wherein the above compound is represented by general formula (2):

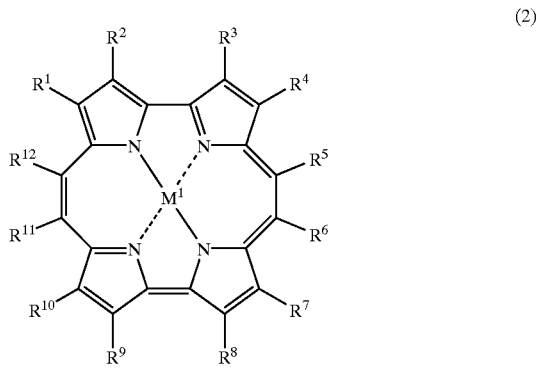

(2)

wherein $R^1$ to $R^{12}$ independently represent hydrogen, halogen, nitro, cyano, hydroxyl, amino, carboxyl, mercapto, substituted or unsubstituted alkyl, aralkyl, aryl, alkenyl, alkoxy, aralkyloxy, aryloxy, alkenyloxy, alkylthio, aralkylthio, arylthio, alkenylthio, acyl, acyloxy, monosubstituted amino, di-substituted amino, alkoxycarbonyl, aralkyloxycarbonyl, aryloxycarbonyl, alkenyloxycarbonyl, mono-substituted aminocarbonyl, di-substituted aminocarbonyl, heteroaryl or heteroaryloxy; or each substituent of $R^1$ to $R^{12}$ together with an adjacent substituent may form a ring through a linking group; and $M^1$ represents two hydrogen atoms, a bivalent to tetravalent metal, metalloid or oxymetal atom optionally having a substituent or ligand.

(5) The above optical recording medium wherein the above compound is represented by general formula (3):

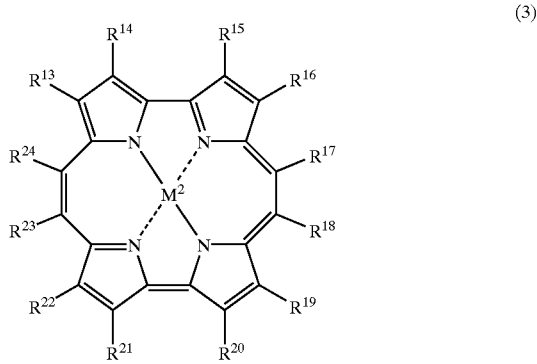

(3)

wherein $R^{13}$ to $R^{24}$ independently represent hydrogen, halogen, nitro, cyano, hydroxyl, amino, carboxyl, mercapto, substituted or unsubstituted alkyl, aralkyl, aryl, alkenyl, alkoxy, aralkyloxy, aryloxy, alkenyloxy, alkylthio, aralkylthio, arylthio, alkenylthio, acyl, acyloxy, monosubstituted amino, di-substituted amino, alkoxycarbonyl, aralkyloxycarbonyl, aryloxycarbonyl, alkenyloxycarbonyl, mono-substituted aminocarbonyl, di-substituted aminocarbonyl, heteroaryl or heteroaryloxy; each of $R^{13}$ to $R^{24}$ together with an adjacent substituent may form a ring through a linking group; $M^2$ is a bivalent to tetravalent metal atom having a substituent selected from the group consisting of alkyl, aryl and heteroaryloxy group and/or a ligand selected from the group consisting of a carbon monoxide and an alcohol.

(6) The above optical recording medium capable of recording and reproduction to a laser beam with a wavelength selected from the range of 300 nm to 500 nm and/or 500 nm to 700 nm.

(7) The above optical recording medium capable of recording and reproduction to a laser beam with a wavelength selected from the range of 400 nm to 500 nm and/or 600 nm to 700 nm.

(8) The above optical recording medium capable of recording and reproduction to a laser beam with a wavelength selected from the range of 400 nm to 410 nm and/or 635 nm to 660 nm.

(9) A compound represented by general formula (1):

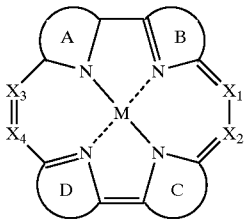

(1)

wherein the rings A, B, C and D independently represent an optionally substituted pyrrole ring; $X^1$, $X^2$, $X^3$ and $X^4$ independently represents optionally substituted methine group; and M represents two hydrogen atoms, a bivalent to tetravalent metal, metalloid or oxymetal atom optionally having substituents or ligands.

(10) The above compound represented by general formula (2):

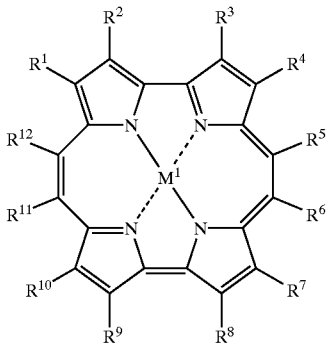

(2)

wherein $R^1$ to $R^{12}$ independently represent hydrogen, halogen, nitro, cyano, hydroxyl, amino, carboxyl, mercapto, substituted or unsubstituted alkyl, aralkyl, aryl, alkenyl, alkoxy, aralkyloxy, aryloxy, alkenyloxy, alkylthio, aralkylthio, arylthio, alkenylthio, acyl, acyloxy, mono-substituted amino, di-substituted amino, alkoxycarbonyl, aralkyloxycarbonyl, aryloxycarbonyl, alkenyloxycarbonyl, mono-substituted aminocarbonyl, di-substituted aminocarbonyl, heteroaryl or heteroaryloxy; or each substituent of $R^1$ to $R^{12}$ together with an adjacent substituent may form a ring through a linking group; and $M_1$ represents two hydrogen atoms, a bivalent to tetravalent metal, metalloid or oxymetal atom optionally having substituents or ligands.

(11) The above compound represented by general formula (3):

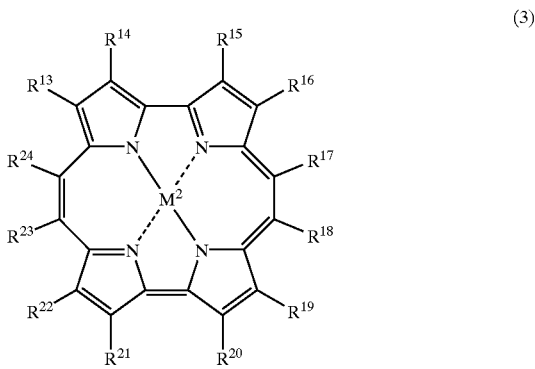

(3)

wherein $R^{13}$ to $R^{24}$ independently represent hydrogen, halogen, nitro, cyano, hydroxyl, amino, carboxyl, mercapto, substituted or unsubstituted alkyl, aralkyl, aryl, alkenyl, alkoxy, aralkyloxy, aryloxy, alkenyloxy, alkylthio, aralkylthio, arylthio, alkenylthio, acyl, acyloxy, mono-substituted amino, di-substituted amino, alkoxycarbonyl, aralkyloxycarbonyl, aryloxycarbonyl, alkenyloxycarbonyl, mono-substituted aminocarbonyl, di-substituted aminocarbonyl, heteroaryl or heteroaryloxy; each of $R^{13}$ to $R^{24}$ together with an adjacent substituent may form a ring through a linking group; $M^2$ is a bivalent to tetravalent metal atom having a substituent selected from the group consisting of alkyl, aryl and heteroaryloxy group and/or a ligand selected from the group consisting of a carbon monoxide and an alcohol.

According to this invention, a porphycene compound of this invention may be used as a dye for a recording layer to provide a recordable optical recording medium capable of recording and reproduction by a laser at 300 to 500 nm, particularly a blue-violet laser at 400 to 410 nm which has drawn much attention in terms of a high-density optical recording medium, as well as capable of recording and reproduction at 500 to 700 nm used for recording a moving picture for two or more hours such as a movie.

DETAILED DESCRIPTION OF THE PREFERRED EMBODIMENTS

This invention relates to an optical recording medium comprising an optionally metal-complexed porphycene compound in its recording layer. In particular, this invention relates to a novel optical recording medium capable of recording and reproduction using a laser beam having a wavelength selected from the range of 300 nm to 500 nm and/or 500 nm to 700 nm, specifically 400 nm to 500 nm and/or 600 to 700 nm, particularly 400 nm to 410 nm and/or 635 nm to 660 nm.

An optical recording medium related to this invention refers to an optical recording medium capable of recording and reproducing information. Herein, there will be described an optical recording medium of this invention as a suitable example comprising a recording layer and a reflecting layer on a substrate. There will be described, as an optical recording medium, an optical disk comprising, for example, a guide groove on a supporting substrate as well as a reflecting film and a recording layer mainly consisting of an organic dye on the groove which conducts recording and reproduction by an ultraviolet/blue laser beam at 300 nm to 500 nm, but an optical recording medium according to this invention should not be limited to such a shape or configuration. Thus, this invention may be applied to a medium having another shape such as a card form and a sheet, a medium without a reflecting layer or a medium employed in recording/reproduction using a laser at a shorter wavelength which will be developed in future.

Figure 1:
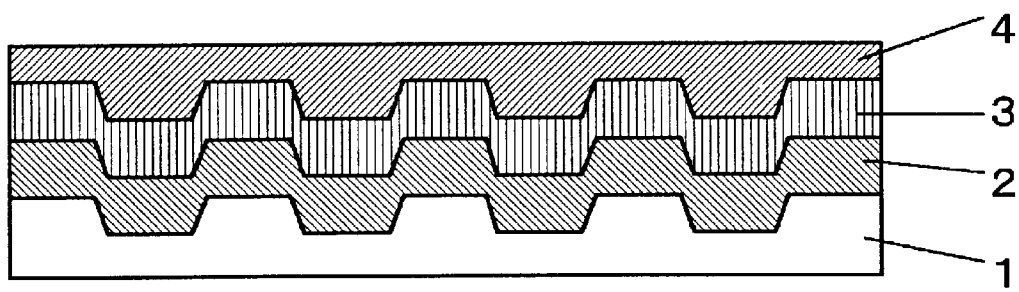
FIG. 1 schematically shows an example for a configuration of an optical recording medium according to this invention.
Figure 2:
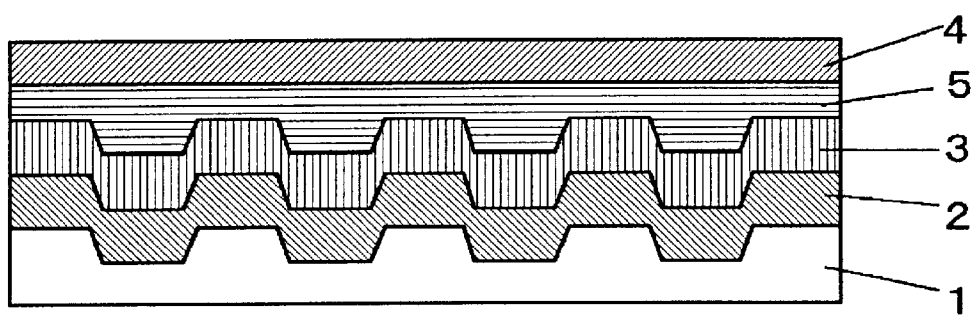
FIG. 2 schematically shows another example for a configuration of an optical recording medium according to this invention.

An optical recording medium according to this invention is of, for example, a four-layered structure as shown in FIG. 1 where a substrate 1, a recording layer 2, a reflecting layer 3 and a protective layer 4 are sequentially laminated, or a laminated structure as shown in FIG. 2 where on a substrate 1 is formed a recording layer 2 on which is closely laminated a reflecting layer 3 on which is further laminated a protective layer 4 via an adhesion layer 5 although there may be another layer on or under the recording layer 2 or on a reflecting layer 3. A structure shown in FIG. 3 may be employed, where a substrate 1, a reflecting layer 3, a recording layer 2 and a protective layer 4 are sequentially laminated and where recording and reproduction may be conducted from the side of the protective layer. Furthermore, a medium structure as described in JP-A 10-326435 where a thickness of a light transmitting layer is defined by an N.A. in an optical system and a laser wavelength λ may be employed. An optical recording medium according to this invention may have, if necessary, a structure comprising at least two recording layers as described in JP-A 11-203729.

Figure 4:
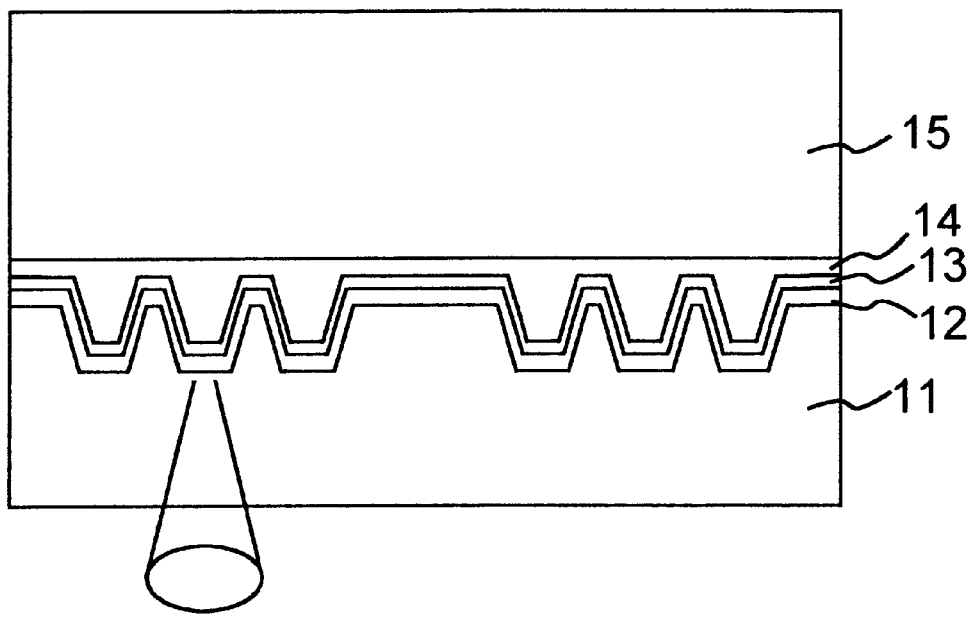
FIG. 4 schematically shows a further example for a configuration of an optical recording medium according to this invention.

This invention may be applied, as shown in FIG. 4, an optical disk where a substrate 11, a recording layer 12, a reflecting layer 13 and a protective layer 14 are sequentially laminated and further a dummy substrate 15 is laminated on the protective layer 14 which also acts as an adhesion layer. Of course, the structure without a substrate 15 may be used and there may be another layer between the recording layer 12 and the reflecting layer 13, between the reflecting layer 13 and the protective layer 14 or between the protective layer 14 and the dummy substrate 15. In the optical disk in FIG. 4, recording and reproduction are conducted from the side of the substrate 11.

Figure 5:
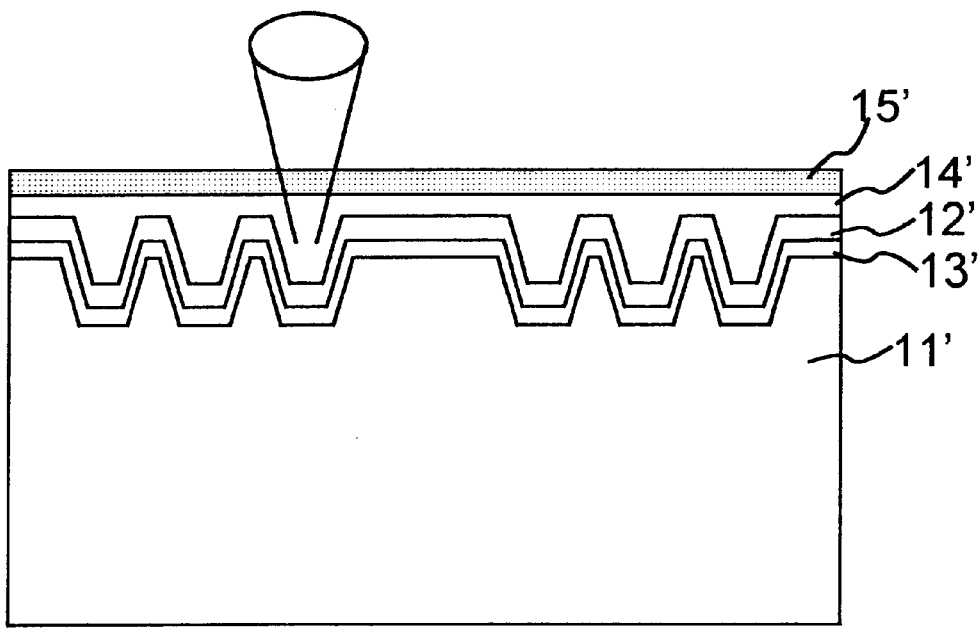
FIG. 5 schematically shows a still further example for a configuration of an optical recording medium according to this invention.
Figures 6A, 6B:
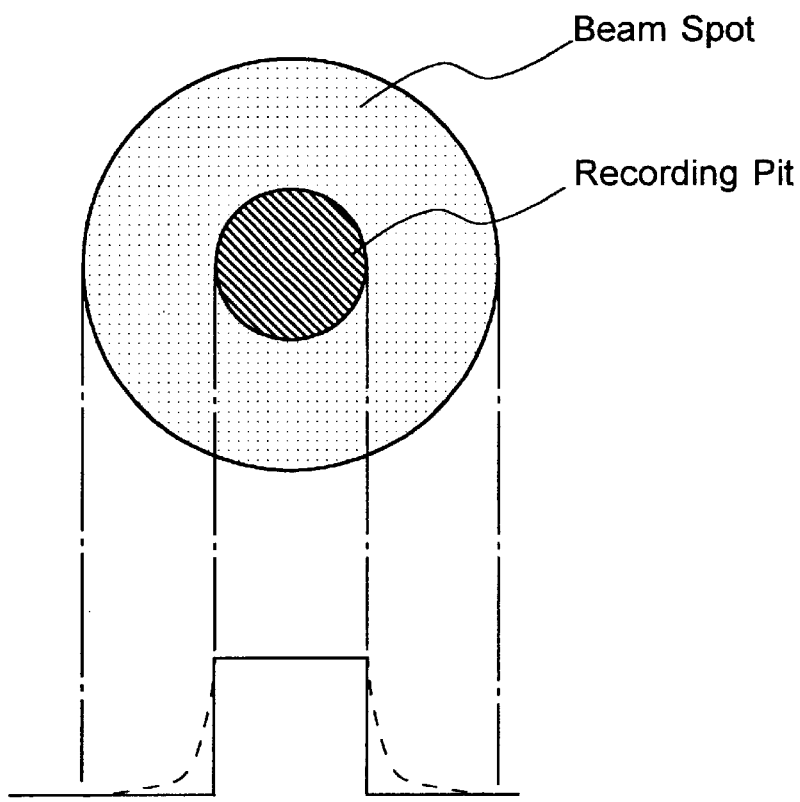
FIGS. 6(a) and 6(b) are conceptual figures illustrating the problems to be solved by this invention.

As another embodiment may be the structure disclosed in JP-A 10-302310, for example, the structure shown in FIG. 5 where on a supporting substrate 11' having a guiding trench are sequentially deposited a reflecting layer 13' and a recording layer 12' mainly comprising an organic dye, on which is formed a light transmitting layer 15' via an optional transparent protective layer 14' and where recording and reproduction of information is conducted from the side of the light transmitting layer 15'. On the contrary, there may be formed a guiding trench in the light transmitting layer 15' on which are then laminated a transparent protective layer 14', a recording layer 12' and a reflecting layer 13', and then the product may be laminated with the supporting substrate 11'.

In this invention, a recording layer is placed on a substrate. The recording layer in this invention comprises at least one optionally metal-complexed porphycene compound, preferably a compound represented by general formula (1), more preferably a compound represented by general formula (2) and the most preferably a compound represented by general formula (3). It can be used to conduct recording and/or reproduction to a recording and/or reproduction laser wavelength selected from the range of 300 nm to 500 nm and/or 500 nm to 700 nm. Particularly, a good C/N ratio may be achieved to a recording and/or reproduction laser wavelength selected from the range of 400 nm to 500 nm and/or 600 to 700 nm, specifically 400 nm to 410 nm and/or 635 nm to 660 nm, and the optical recording medium may exhibit good reproduction light stability and high quality signal properties.

For a compound represented by general formula (1), more preferably a compound represented by general formula (2) and the most preferably a compound represented by general formula (3) herein, a substituent may be selected to appropriately select an absorption wavelength while maintaining an absorption coefficient. It is, therefore, a significantly useful organic dye which may meet optical constants required for a recording layer in the above laser-beam wavelength.

There will be described this invention in detail.

For a compound represented by general formula (1) in this invention, examples of a substituent in an optionally substituted pyrrole ring represented by the ring A, B, C or D include hydrogen, halogen, nitro, cyano, hydroxyl, amino, carboxyl, mercapto, substituted or unsubstituted alkyl, aralkyl, aryl, alkenyl, alkoxy, aralkyloxy, aryloxy, alkenyloxy, alkylthio, aralkylthio, arylthio, alkenylthio, acyl, acyloxy, mono-substituted amino, di-substituted amino, alkoxycarbonyl, aralkyloxycarbonyl, aryloxycarbonyl, alkenyloxycarbonyl, mono-substituted aminocarbonyl, di-substituted aminocarbonyl, heteroaryl and heteroaryloxy.

Examples of a substituent in optionally substituted methine group represented by $X^1$, $X^2$, $X^3$ or $X^4$ in the porphycene structure represented by general formula (1) include optionally substituted methines represented by formulas (4), (5), (6) and (7):

(4)

(5)

(6)

(7)

wherein $G^1$, $G^2$, $G^3$ and $G^4$ are as defined for an optional substituent on the above pyrrole ring.

The substituents on the pyrrole rings may be linked with each other or a substituent on an adjacent methine group represented by $X^1$, $X^2$, $X^3$ and $X^4$ via a linking group.

Specific examples of such a case include ring formation through aliphatic or aromatic condensation and formation of a heterocyclic ring containing at least one hetero atom in which a linking group is a hetero atom, a metal complex residue or the like.

M in general formula (1) represents two hydrogen atoms, a bivalent to tetravalent metal or metalloid atom optionally having a substituent. Examples of the metal or metalloid atom include bivalent metal atoms, substituted trivalent or tetravalent metal or metalloid atoms and oxymetal groups.

A preferable compound represented by general formula (1) in this invention is a compound represented by general formula (2):

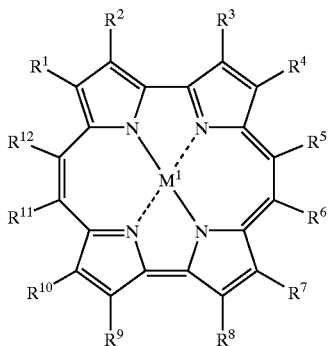

(2)

wherein $R^1$ to $R^{12}$ independently represent hydrogen, halogen, nitro, cyano, hydroxyl, amino, carboxyl, mercapto, substituted or unsubstituted alkyl, aralkyl, aryl, alkenyl, alkoxy, aralkyloxy, aryloxy, alkenyloxy, alkylthio, aralkylthio, arylthio, alkenylthio, acyl, acyloxy, mono-substituted amino, di-substituted amino, alkoxycarbonyl, aralkyloxycarbonyl, aryloxycarbonyl, alkenyloxycarbonyl, mono-substituted aminocarbonyl, di-substituted aminocarbonyl, heteroaryl or heteroaryloxy; each substituent of $R^1$ to $R^{12}$ together with an adjacent substituent may form a ring via a linker; Mrepresents two hydrogens, a bivalent to tetravalent metal, metalloid or oxymetal atom optionally having a substituent or ligand.

Examples of $R^1$ to $R^{12}$ in the compound represented by general formula (2) of this invention include hydrogen; halogens such as fluorine, chlorine, bromine and iodine; nitro; cyano; hydroxyl; amino; carboxyl; and mercapto.

Examples of a substituted or unsubstituted alkyl for $R^1$ to $R^{12}$ include unsubstituted straight, branched or circular alkyl having 1 to 15 carbon atoms such as methyl, ethyl, n-propyl, iso-propyl, n-butyl, iso-butyl, sec-butyl, t-butyl, n-pentyl, iso-pentyl, 2-methylbutyl, 1-methylbutyl, neopentyl, 1,2-dimethylpropyl, 1,1-dimethylpropyl, cyclopentyl, n-hexyl, 4-methylpentyl, 3-methylpentyl, 2-methylpentyl, 1-methylpentyl, 3,3-dimethylbutyl, 2,3-dimethylbutyl, 1,3-dimethylbutyl, 2,2-dimethylbutyl, 1,2-dimethylbutyl, 1,1-dimethylbutyl, 3-ethylbutyl, 2-ethylbutyl, 1-ethylbutyl, 1,2,2-trimethylbutyl, 1,1,2-trimethylbutyl, 1-ethyl-2-methylpropyl, cyclohexyl, n-heptyl, 2-methylhexyl, 3-methylhexyl, 4-methylhexyl, 5-methylhexyl, 2,4-dimethylpentyl, n-octyl, 2-ethylhexyl, 2,5-dimethylhexyl, 2,5,5-trimethylpentyl, 2,4-dimethylhexyl, 2,2,4-trimethylpentyl, 3,5,5-trimethylhexyl, n-nonyl, n-decyl, 4-ethyloctyl, 4-ethyl-4,5-methylhexyl, n-undecyl, n-dodecyl, 1,3,5,7-tetraethyloctyl, 4-butyloctyl, 6,6-diethyloctyl, n-tridecyl, 6-methyl-4-butyloctyl, n-tetradecyl, n-pentadecyl, 3,5-dimethylheptyl, 2,6-dimethylheptyl, 2,4-dimethylheptyl, 2,2,5,5-tetramethylhexyl, 1-cyclopentyl-2,2-dimethylpropyl and 1-cyclohexyl-2,2-dimethylpropyl;

halogenated alkyl having 1 to 10 carbon atoms such as chloromethyl, chloroethyl, bromoethyl, iodoethyl, dichloromethyl, fluoromethyl, trifluoromethyl, pentafluoroethyl, 2,2,2-trifluoroethyl, 2,2,2-trichloroethyl, 1,1,1,3,3,3-hexafluoro-2-propyl, nonafluorobutyl and perfluorodecyl;

hydroxyl-alkyl having 1 to 10 carbon atoms such as hydroxymethyl, 2-hydroxyethyl, 3-hydroxypropyl, 4-hydroxybutyl, 2-hydroxy-3-methoxypropyl, 2-hydroxy-3-chloropropyl, 2-hydroxy-3-ethoxypropyl, 3-butoxy-2-hydroxypropyl, 2-hydroxy-3-cyclohexyloxypropyl, 2-hydroxypropyl, 2-hydroxybutyl and 4-hydroxydecalyl;

hydroxyalkoxy-alkyl having 2 to 10 carbon atoms such as hydroxymethoxymethyl, hydroxyethoxyethyl, 2-(2'-hydroxy-1'-methylethoxy)-1-methylethyl, 2-(3'-fluoro-2'-hydroxypropoxy)ethyl, 2-(3'-chloro-2'-hydroxypropoxy)ethyl and hydroxybutoxycyclohexyl;

hydroxyalkoxyalkoxy-alkyl having 3 to 10 carbon atoms such as hydroxymethoxymethoxymethyl, hydroxyethoxyethoxyethyl, [2'-(2'-hydroxy-1'-methylethoxy)-1'-methylethoxy]ethoxyethyl, [2'-(2'-fluoro-1'-hydroxyethoxy)-1'-methylethoxy]ethoxyethyl and [2'-(2'-chloro-1'-hydroxyethoxy)-1'-methylethoxy]ethoxyethyl;

cyanoalkyl having 2 to 10 carbon atoms such as cyanomethyl, 2-cyanoethyl, 3-cyanopropyl, 4-cyanobutyl, 2-cyano-3-methoxypropyl, 2-cyano-3-chloropropyl, 2-cyano-3-ethoxypropyl, 3-butoxy-2-cyanopropyl, 2-cyano-3-cyclohexylpropyl, 2-cyanopropyl and 2-cyanobutyl;

alkoxy-alkyl having 2 to 15 carbon atoms such as methoxymethyl, ethoxymethyl, propoxymethyl, butoxymethyl, methoxyethyl, ethoxyethyl, propoxyethyl, butoxyethyl, n-hexyloxyethyl, (4-methylpentoxy)ethyl, (1,3-dimethylbutoxy)ethyl, (2-ethylhexyloxy)ethyl, n-octyloxyethyl, (3,5,5-trimethylhexyloxy)ethyl, (2-methyl-1-iso-propylpropoxy)ethyl, (3-methyl-1-iso-propylbutyloxy)ethyl, 2-ethoxy-1-methylethyl, 3-methoxybutyl, (3,3,3-trifluoropropoxy)ethyl and (3,3,3-trichloropropoxy)ethyl;

alkoxyalkoxy-alkyl having 3 to 15 carbon atoms such as methoxymethoxymethyl, methoxyethoxyethyl, ethoxyethoxyethyl, propoxyethoxyethyl, butoxyethoxyethyl, cyclohexyloxyethoxyethyl, decyloxypropoxyethoxyethyl, (1,2-dimethylpropoxy)ethoxyethyl, (3-methyl-1-iso-butylbutoxy)ethoxyethyl, (2-methoxy-1-methylethoxy)ethyl, (2-butoxy-1-methylethoxy)ethyl, 2-(2'-ethoxy-1'-methylethoxy)-1-methylethyl, (3,3,3-trifluoropropoxy)ethoxyethyl and (3,3,3-trichloropropoxy)ethoxyethyl;

alkoxyalkoxyalkoxy-alkyl having 4 to 15 carbons such as methoxymethoxymethoxymethyl, methoxyethoxyethoxyethyl, ethoxyethoxyethoxyethyl, butoxyethoxyethoxyethyl, cyclohexyloxyethoxyethoxyethyl, propoxypropoxypropoxyethyl, (2,2,2-trifluoroethoxy)ethoxyethoxyethyl and (2,2,2-trichloroethoxy)ethoxyethoxyethyl;

acyl-alkyl having 2 to 10 carbon atoms such as formylmethyl, 2-oxobutyl, 3-oxobutyl, 4-oxobutyl, 2,6-dioxocyclohexane-1-yl and 2-oxo-5-t-butylcyclohexane-1-yl;

acyloxy-alkyl having 2 to 15 carbon atoms such as formyloxymethyl, acetoxyethyl, propionyloxyethyl, butanoyloxyethyl, valeryloxyethyl, (2-ethylhexanoyloxy)ethyl, (3,5,5-trimethylhexanoyloxy)ethyl, (3,5,5-trimethylhexanoyloxy)hexyl, (3-fluorobutylyloxy)ethyl and (3-chlorobutylyloxy)ethyl;

acyloxyalkoxy-alkyl having 3 to 15 carbon atoms such as formyloxymethoxymethyl, acetoxyethoxyethyl, propionyloxyethoxyethyl, valeryloxyethoxyethyl, (2-ethylhexanoyloxy)ethoxyethyl, (3,5,5-trimethylhexanoyloxy)butoxyethyl, (3,5,5-trimethylhexanoyloxy)ethoxyethyl, (2-fluoropropionyloxy)ethoxyethyl and (2-chloropropionyloxy)ethoxyethyl;

acyloxyalkoxyalkoxy-alkyl having 5 to 15 carbon atoms such as acetoxymethoxymethoxymethyl, acetoxyethoxyethoxyethyl, propionyloxyethoxyethoxyethyl, valeryloxyethoxyethoxyethyl, (2-ethylhexanoyloxy)ethoxyethoxyethyl, (3,5,5-trimethylhexanoyloxy)ethoxyethoxyethyl, (2-fluoropropionyloxy)ethoxyethoxyethyl and (2-chloropropionyloxy)ethoxyethoxyethyl;

alkoxycarbonyl-alkyl having 3 to 15 carbon atoms such as methoxycarbonylmethyl, ethoxycarbonylmethyl, butoxycarbonylmethyl, methoxycarbonylethyl, ethoxycarbonylethyl, butoxycarbonylethyl, (p-ethylcyclohexyloxycarbonyl)cyclohexyl, (2,2,3,3-tetrafluoropropoxycarbonyl)methyl and (2,2,3,3-tetrachloropropoxycarbonyl)methyl;

aryloxycarbonyl-alkyl having 8 to 15 carbon atoms such as phenoxycarbonylmethyl, phenoxycarbonylethyl, (4-t-butylphenoxycarbonyl)ethyl, naphthyloxycarbonylmethyl and biphenyloxycarbonylethyl;

aralkyloxycarbonyl-alkyl having 9 to 15 carbon atoms such as benzyloxycarbonylmethyl, benzyloxycarbonylethyl, phenetyloxycarbonylmethyl and (4-cyclohexyloxybenzyloxycarbonyl)methyl;

alkenyloxycarbonyl-alkyl having 4 to 10 carbon atoms such asvinyloxycarbonylmethyl, vinyloxycarbonylethyl, allyloxycarbonylmethyl, cyclopentadienyloxycarbonylmethyl and octenoxycarbonylmethyl;

alkoxycarbonyloxy-alkyl having 3 to 15 carbon atoms such as methoxycarbonyloxymethyl, methoxycarbonyloxyethyl, ethoxycarbonyloxyethyl, butoxycarbonyloxyethyl, (2,2,2-trifluoroethoxycarbonyloxy)ethyl and (2,2,2-trichloroethoxycarbonyloxy)ethyl;

alkoxyalkoxycarbonyloxy-alkyl having 4 to 15 carbon atoms such as methoxymethoxycarbonyloxymethyl, methoxyethoxycarbonyloxyethyl, ethoxyethoxycarbonyloxyethyl, butoxyethoxycarbonyloxyethyl, (2,2,2-trifluoroethoxy)ethoxycarbonyloxyethyl and (2,2,2-trichloroethoxy)ethoxycarbonyloxyethyl;

dialkylamino-alkyl having 3 to 20 carbon atoms such as dimethylaminomethyl, diethylaminomethyl, di-n-butylaminomethyl, di-n-hexylaminomethyl, di-n-octylaminomethyl, di-n-decylaminomethyl, N-isoamyl-N-methylaminomethyl, piperidinomethyl, di(methoxymethyl)aminomethyl, di(methoxyethyl) aminomethyl, di(ethoxymethyl)aminomethyl, di(ethoxyethyl)aminomethyl, di(propoxyethyl)aminomethyl, di(butoxyethyl)aminomethyl, bis(2-cyclohexyloxyethyl)aminomethyl, dimethylaminoethyl, diethylaminoethyl, di-n-butylaminoethyl, di-n-hexylaminoethyl, di-n-octylaminoethyl, di-n-decylaminoethyl, N-isoamyl-N-methylaminoethyl, piperidinoethyl, di(methoxymethyl)aminoethyl, di(methoxyethyl) aminoethyl, di(ethoxymethyl)aminoethyl, di(ethoxyethyl)aminoethyl, di(propoxyethyl)aminoethyl, di(butoxyethyl)aminoethyl, bis(2-cyclohexyloxyethyl)aminoethyl, dimethylaminopropyl, diethylaminopropyl, di-n-butylaminopropyl, di-n-hexylaminopropyl, di-n-octylaminopropyl, di-n-decylaminopropyl, N-isoamyl-N-methylaminopropyl, piperidinopropyl, di(methoxymethyl)aminopropyl, di(methoxyethyl) aminopropyl, di(ethoxymethyl)aminopropyl, di(ethoxyethyl)aminopropyl, di(propoxyethyl)aminopropyl, di(butoxyethyl)aminopropyl, bis(2-cyclohexyloxyethyl)aminopropyl, dimethylaminobutyl, diethylaminobutyl, di-n-butylaminobutyl, di-n-hexylaminobutyl, di-n-octylaminobutyl, di-n-decylaminobutyl, N-isoamyl-N-methylaminobutyl, piperidinobutyl, di(methoxymethyl)aminobutyl, di(methoxyethyl) aminobutyl, di(ethoxymethyl)aminobutyl, di(methoxyethyl)aminobutyl, di(propoxyethyl) aminobutyl, di(butoxyethyl)aminobutyl and bis(2-cyclohexyloxyethyl)aminobutyl;

acylamino-alkyl having 3 to 10 carbon atoms such as acetylaminomethyl, acetylaminoethyl, propionylaminoethyl, butanoylaminoethyl, cyclohexanecarbonylaminoethyl, p-methylcyclohexanecarbonylaminoethyl and succiniminoethyl;

alkylsulfonamino-alkyl having 2 to 10 carbon atoms such as methylsulfonaminomethyl, methylsulfonaminoethyl, ethylsulfonaminoethyl, propylsulfonaminoethyl and octylsulfonaminoethyl;

alkylsulfonyl-alkyl having 2 to 10 carbon atoms such as methylsulfonylmethyl, ethylsulfonylmethyl, butylsulfonylmethyl, methylsulfonylethyl, ethylsulfonylethyl, butylsulfonylethyl, 2-ethylhexylsulfonylethyl, 2,2,3,3-tetrafluoropropylsulfonylmethyl and 2,2,3,3-tetrachloropropylsulfonylmethyl;

arylsulfonyl-alkyl having 7 to 12 carbon atoms such as benzenesulfonylmethyl, benzenesulfonylethyl, benzenesulfonylpropyl, benzenesulfonylbutyl, toluenesulfonylmethyl, toluenesulfonylethyl, toluenesulfonylpropyl, toluenesulfonylbutyl, xylenesulfonylmethyl, xylenesulfonylethyl, xylenesulfonylpropyl and xylenesulfonylbutyl;

heterocycle-substituted alkyl having 2 to 13 carbon atoms such as thiadiazolinomethyl, pyrrolinomethyl, pyrrolidinomethyl, pyrazolidinomethyl, imidazolidinomethyl, oxazolylmethyl, triazolinomethyl, morpholinomethyl, indolinomethyl, benzimidazolinomethyl and carbazolinomethyl;

metallocenyl-alkyl having 11 to 20 carbon atoms such as ferrocenylmethyl, ferrocenylethyl, ferrocenyl-n-propyl, ferrocenyl-iso-propyl, ferrocenyl-n-butyl, ferrocenyl-iso-butyl, ferrocenyl-sec-butyl, ferrocenyl-t-butyl, ferrocenyl-n-pentyl, ferrocenyl-iso-pentyl, ferrocenyl-2-methylbutyl, ferrocenyl-1-methylbutyl, ferrocenylneopentyl, ferrocenyl-1,2-dimethylpropyl, ferrocenyl-1,1-dimethylpropyl, ferrocenylcyclopentyl, ferrocenyl-n-hexyl, ferrocenyl-4-methylpentyl, ferrocenyl-3-methylpentyl, ferrocenyl-2-methylpentyl, ferrocenyl-1-methylpentyl, ferrocenyl-3,3-dimethylbutyl, ferrocenyl-2,3-dimethylbutyl, ferrocenyl-1,3-dimethylbutyl, ferrocenyl-2,2-dimethylbutyl, ferrocenyl-1,2-dimethylbutyl, ferrocenyl-1,1-dimethylbutyl, ferrocenyl-3-ethylbutyl, ferrocenyl-2-ethylbutyl, ferrocenyl-1-ethylbutyl, ferrocenyl-1,2,2-trimethylbutyl, ferrocenyl-1,1,2-trimethylbutyl, ferrocenyl-1-ethyl-2-methylpropyl, ferrocenylcyclohexyl, ferrocenyl-n-heptyl, ferrocenyl-2-methylhexyl, ferrocenyl-3-methylhexyl, ferrocenyl-4-methylhexyl, ferrocenyl-5-methylhexyl, ferrocenyl-2,4-dimethylpentyl, ferrocenyl-n-octyl, ferrocenyl-2-ethylhexyl, ferrocenyl-2,5-dimethylhexyl, ferrocenyl-2,5,5-trimethylpentyl, ferrocenyl-2,4-dimethylhexyl, ferrocenyl-2,2,4-trimethylpentyl, ferrocenyl-3,5,5-trimethylhexyl, ferrocenyl-n-nonyl, ferrocenyl-n-decyl, cobaltocenylmethyl, cobaltocenylethyl, cobaltocenyl-n-propyl, cobaltocenyl-iso-propyl, cobaltocenyl-n-butyl, cobaltocenyl-iso-butyl, cobaltocenyl-sec-butyl, cobaltocenyl-t-butyl, cobaltocenyl-n-pentyl, cobaltocenyl-iso-pentyl, cobaltocenyl-2-methylbutyl, cobaltocenyl-1-methylbutyl, cobaltocenylneopentyl, cobaltocenyl-1,2-dimethylpropyl, cobaltocenyl-1,1-dimethylpropyl, cobaltocenylcyclopentyl, cobaltocenyl-n-hexyl, cobaltocenyl-4-methylpentyl, cobaltocenyl-3-methylpentyl, cobaltocenyl-2-methylpentyl, cobaltocenyl-1-methylpentyl, cobaltocenyl-3,3-dimethylbutyl, cobaltocenyl-2,3-dimethylbutyl, cobaltocenyl-1,3-dimethylbutyl, cobaltocenyl-2,2-dimethylbutyl, cobaltocenyl-1,2-dimethylbutyl, cobaltocenyl-1,1-dimethylbutyl, cobaltocenyl-3-ethylbutyl, cobaltocenyl-2-ethylbutyl, cobaltocenyl-1-ethylbutyl, cobaltocenyl-1,2,2-trimethylbutyl, cobaltocenyl-1,1,2-trimethylbutyl, cobaltocenyl-1-ethyl-2-methylpropyl, cobaltocenylcyclohexyl, cobaltocenyl-n-heptyl, cobaltocenyl-2-methylhexyl, cobaltocenyl-3-methylhexyl, cobaltocenyl-4-methylhexyl, cobaltocenyl-5-methylhexyl, cobaltocenyl-2,4-dimethylpentyl, cobaltocenyl-n-octyl, cobaltocenyl-2-ethylhexyl, cobaltocenyl-2,5-dimethylhexyl, cobaltocenyl-2,5,5-trimethylpentyl, cobaltocenyl-2,4-dimethylhexyl, cobaltocenyl-2,2,4-trimethylpentyl, cobaltocenyl-3,5,5-trimethylhexyl, cobaltocenyl-n-nonyl, cobaltocenyl-n-decyl, nickelocenylmethyl, nickelocenylethyl, nickelocenyl-n-propyl, nickelocenyl-iso-propyl, nickelocenyl-n-butyl, nickelocenyl-iso-butyl, nickelocenyl-sec-butyl, nickelocenyl-t-butyl, nickelocenyl-n-pentyl, nickelocenyl-iso-pentyl, nickelocenyl-2-methylbutyl, nickelocenyl-1-methylbutyl, nickelocenylneopentyl, nickelocenyl-1,2-dimethylpropyl, nickelocenyl-1,1-dimethylpropyl, nickelocenylcyclopentyl, nickelocenyl-n-hexyl, nickelocenyl-4-methylpentyl, nickelocenyl-3-methylpentyl, nickelocenyl-2-methylpentyl, nickelocenyl-1-methylpentyl, nickelocenyl-3,3-dimethylbutyl, nickelocenyl-2,3-dimethylbutyl, nickelocenyl-1,3-dimethylbutyl, nickelocenyl-2,2-dimethylbutyl, nickelocenyl-1,2-dimethylbutyl, nickelocenyl-1,1-dimethylbutyl, nickelocenyl-3-ethylbutyl, nickelocenyl-2-ethylbutyl, nickelocenyl-1-ethylbutyl, nickelocenyl-1,2,2-trimethylbutyl, nickelocenyl-1,1,2-trimethylbutyl, nickelocenyl-1-ethyl-2-methylpropyl, nickelocenylcyclohexyl, nickelocenyl-n-heptyl, nickelocenyl-2-methylhexyl, nickelocenyl-3-methylhexyl, nickelocenyl-4-methylhexyl, nickelocenyl-5-methylhexyl, nickelocenyl-2,4-dimethylpentyl, nickelocenyl-n-octyl, nickelocenyl-2-ethylhexyl, nickelocenyl-2,5-dimethylhexyl, nickelocenyl-2,5,5-trimethylpentyl, nickelocenyl-2,4-dimethylhexyl, nickelocenyl-2,2,4-trimethylpentyl, nickelocenyl-3,5,5-trimethylhexyl, nickelocenyl-n-nonyl, nickelocenyl-n-decyl, dichlorotitanocenylmethyl, trichlorotitaniumcyclopentadienylmethyl, bis(trifluoromethanesulfonato)titanocenemethyl, dichlorozirconocenylmethyl, dimethylzirconocenylmethyl, diethoxyzirconocenylmethyl, bis(cyclopentadienyl)chromium-methyl, bis(cyclopentadienyl)dichloromolybdenum-methyl, bis(cyclopentadienyl)dichlorohafnium-methyl, bis(cyclopentadienyl)dichloroniobium-methyl, bis(cyclopentadienyl)ruthenium-methyl, bis(cyclopentadienyl)vanadium-methyl and bis(cyclopentadienyl)dichlorovanadium-methyl;

metallocenylalkyloxy-alkyl having 12 to 30 carbon atoms such as ferrocenylmethoxymethyl, ferrocenylmethoxyethyl, ferrocenylmethoxypropyl, ferrocenylmethoxybutyl, ferrocenylmethoxypentyl, ferrocenylmethoxyhexyl, ferrocenylmethoxyheptyl, ferrocenylmethoxyoctyl, ferrocenylmethoxynonyl, ferrocenylmethoxydecyl, ferrocenylethoxymethyl, ferrocenylethoxyethyl, ferrocenylethoxypropyl, ferrocenylethoxybutyl, ferrocenylethoxypentyl, ferrocenylethoxyhexyl, ferrocenylethoxyheptyl, ferrocenylethoxyoctyl, ferrocenylethoxynonyl, ferrocenylethoxydecyl, ferrocenylpropoxymethyl, ferrocenylpropoxyethyl, ferrocenylpropoxypropyl, ferrocenylpropoxybutyl, ferrocenylpropoxypentyl, ferrocenylpropoxyhexyl, ferrocenylpropoxyheptyl, ferrocenylpropoxyoctyl, ferrocenylpropoxynonyl, ferrocenylpropoxydecyl, ferrocenylbutoxymethyl, ferrocenylbutoxyethyl, ferrocenylbutoxypropyl, ferrocenylbutoxybutyl, ferrocenylbutoxypentyl, ferrocenylbutoxyhexyl, ferrocenylbutoxyheptyl, ferrocenylbutoxyoctyl, ferrocenylbutoxynonyl, ferrocenylbutoxydecyl, ferrocenyldecyloxymethyl, ferrocenyldecyloxyethyl, ferrocenyldecyloxypropyl, ferrocenyldecyloxybutyl, ferrocenyldecyloxypentyl, ferrocenyldecyloxyhexyl, ferrocenyldecyloxyheptyl, ferrocenyldecyloxyoctyl, ferrocenyldecyloxynonyl, ferrocenyldecyloxydecyl, cobaltocenylmethoxymethyl, cobaltocenylmethoxyethyl, cobaltocenylmethoxypropyl, cobaltocenylmethoxybutyl, cobaltocenylmethoxypentyl, cobaltocenylmethoxyhexyl, cobaltocenylmethoxyheptyl, cobaltocenylmethoxyoctyl, cobaltocenylmethoxynonyl, cobaltocenylmethoxydecyl, cobaltocenylethoxymethyl, cobaltocenylethoxyethyl, cobaltocenylethoxypropyl, cobaltocenylethoxybutyl, cobaltocenylethoxypentyl, cobaltocenylethoxyhexyl, cobaltocenylethoxyheptyl, cobaltocenylethoxyoctyl, cobaltocenylethoxynonyl, cobaltocenylethoxydecyl, cobaltocenylpropoxymethyl,
cobaltocenylpropoxyethyl,
cobaltocenylpropoxypropyl,
cobaltocenylpropoxybutyl,
cobaltocenylpropoxypentyl,
cobaltocenylpropoxyhexyl,
cobaltocenylpropoxyheptyl,
cobaltocenylpropoxyoctyl, cobaltocenylpropoxynonyl, cobaltocenylpropoxydecyl, cobaltocenylbutoxymethyl, cobaltocenylbutoxyethyl, cobaltocenylbutoxypropyl, cobaltocenylbutoxybutyl, cobaltocenylbutoxypentyl, cobaltocenylbutoxyhexyl, cobaltocenylbutoxyheptyl, cobaltocenylbutoxyoctyl, cobaltocenylbutoxynonyl,
cobaltocenylbutoxydecyl,
cobaltocenyldecyloxymethyl,
cobaltocenyldecyloxyethyl,
cobaltocenyldecyloxypropyl,
cobaltocenyldecyloxybutyl,
cobaltocenyldecyloxypentyl,
cobaltocenyldecyloxyhexyl,
cobaltocenyldecyloxyheptyl,
cobaltocenyldecyloxyoctyl,
cobaltocenyldecyloxynonyl,
cobaltocenyldecyloxydecyl, nickelocenylmethoxymethyl, nickelocenylmethoxyethyl,
nickelocenylmethoxypropyl,
nickelocenylmethoxybutyl,
nickelocenylmethoxypentyl,
nickelocenylmethoxyhexyl,
nickelocenylmethoxyheptyl,
nickelocenylmethoxyoctyl,
nickelocenylmethoxynonyl,
nickelocenylmethoxydecyl,
nickelocenylethoxymethyl, nickelocenylethoxyethyl, nickelocenylethoxypropyl, nickelocenylethoxybutyl, nickelocenylethoxypentyl, nickelocenylethoxyhexyl, nickelocenylethoxyheptyl, nickelocenylethoxyoctyl, nickelocenylethoxynonyl, nickelocenylethoxydecyl,
nickelocenylpropoxymethyl,
nickelocenylpropoxyethyl,
nickelocenylpropoxypropyl,
nickelocenylpropoxybutyl,
nickelocenylpropoxypentyl,
nickelocenylpropoxyhexyl,
nickelocenylpropoxyheptyl,
nickelocenylpropoxyoctyl, nickelocenylpropoxynonyl, nickelocenylpropoxydecyl, nickelocenylbutoxymethyl, nickelocenylbutoxyethyl, nickelocenylbutoxypropyl, nickelocenylbutoxybutyl, nickelocenylbutoxypentyl, nickelocenylbutoxyhexyl, nickelocenylbutoxyheptyl, nickelocenylbutoxyoctyl, nickelocenylbutoxynonyl,
nickelocenylbutoxydecyl,
nickelocenyldecyloxymethyl,
nickelocenyldecyloxyethyl,
nickelocenyldecyloxypropyl,
nickelocenyldecyloxybutyl,
nickelocenyldecyloxypentyl, nickelocenyldecyloxyhexyl nickelocenyldecyloxyheptyl,
nickelocenyldecyloxyoctyl,
nickelocenyldecyloxynonyl,
nickelocenyldecyloxydecyl, dichlorotitanocenylmethoxymethyl,
trichlorotitaniumcyclopentadienylmethoxyethyl, bis(trifluoromethanesulfonato)titanocenemethoxypropyl,
dichlorozirconocenylmethoxybutyl,
dimethylzirconocenylmethoxypentyl,
diethoxyzirconocenylmethoxymethyl, bis(cyclopentadienyl)chromium-methoxyhexyl, bis(cyclopentadienyl)dichlorohafnium-methoxymethyl, bis(cyclopentadienyl)dichloroniobium-methoxyoctyl, bis(cyclopentadienyl)niobium-methoxymethyl, bis(cyclopentadienyl)vanadium-methoxymethyl, bis(cyclopentadienyl)dichlorovanadium-methoxyethyl and osmocenylmethoxyethyl;

metallocenylcarbonyloxy-alkyl having 12 to 30 carbon atoms such as ferrocenecarbonyloxymethyl,
ferrocenecarbonyloxyethyl,
ferrocenecarbonyloxypropyl,
ferrocenecarbonyloxybutyl,
ferrocenecarbonyloxypentyl,
ferrocenecarbonyloxyhexyl,
ferrocenecarbonyloxyheptyl,
ferrocenecarbonyloxyoctyl,
ferrocenecarbonyloxynonyl,
ferrocenecarbonyloxydecyl,
cobaltocenecarbonyloxymethyl,
cobaltocenecarbonyloxyethyl,
cobaltocenecarbonyloxypropyl,
cobaltocenecarbonyloxybutyl,
cobaltocenecarbonyloxypentyl,
cobaltocenecarbonyloxyhexyl,
cobaltocenecarbonyloxyheptyl,
cobaltocenecarbonyloxyoctyl,
cobaltocenecarbonyloxynonyl,
cobaltocenecarbonyloxydecyl,
nickelocenecarbonyloxymethyl,
nickelocenecarbonyloxyethyl,
nickelocenecarbonyloxypropyl,
nickelocenecarbonyloxybutyl,
nickelocenecarbonyloxypentyl,
nickelocenecarbonyloxyhexyl,
nickelocenecarbonyloxyheptyl,
nickelocenecarbonyloxyoctyl,
nickelocenecarbonyloxynonyl,
nickelocenecarbonyloxydecyl,
dichlorotitanocenylcarbonyloxymethyl,
trichlorotitaniumcyclopentadienylcarbonyloxyethyl,
bis(trifluoromethanesulfonate)titanocenecarbonyloxymethoxy propyl,
dichlorozirconocenecarbonyloxybutyl,
dimethylzirconocenecarbonyloxypentyl,
diethoxyzirconocenecarbonyloxymethyl, bis(cyclopentadienyl)chromiumcarbonyloxyhexyl, bis(cyclopentadienyl)dichlorohafniumcarbonyloxymethyl, bis(cyclopentadienyl)dichloroniobiumcarbonyloxyoctyl, bis(cyclopentadienyl)niobiumcarbonyloxymethyl, bis(cyclopentadienyl)vanadiumcarbonyloxymethyl, bis(cyclopentadienyl)dichlorovanadiumcarbonyloxyethyl and bis(cyclopentadienyl)osmiumcarbonyloxyethyl.

Examples of substituted or unsubstituted aralkyl for $R^1$ to $R^{12}$ include aralkyl optionally substituted as described above for alkyl; preferably aralkyl having 7 to 15 carbon atoms such as benzyl, nitrobenzyl, cyanobenzyl, hydroxybenzyl, methylbenzyl, trifluoromethylbenzyl, naphthylmethyl, nitronaphthylmethyl, cyanonaphthylmethyl, hydroxynaphthylmethyl, methylnaphthylmethyl, trifluoromethylnaphthylmethyl and fluoren-9-ylethyl.

Examples of substituted or unsubstituted aryl for $R^1$ to $R^{12}$ include aryl optionally substituted as described above for alkyl; preferably aryl having 6 to 15 carbon atoms such as phenyl, nitrophenyl, cyanophenyl, hydroxyphenyl, methylphenyl, trifluoromethylphenyl, naphthyl, nitronaphthyl, cyanonaphthyl, hydroxynaphthyl, methylnaphthyl, trifluoromethylnaphthyl, methoxycarbonylphenyl, 4-(5'-methylbenzoxazol-2'-yl)phenyl and dibutylaminocarbonylphenyl.

Examples of substituted or unsubstituted alkenyl for $R^1$ to $R^{12}$ include alkenyl optionally substituted as described above for alkyl; preferably alkenyl having 2 to 10 carbon atoms such as vinyl, propenyl, 1-butenyl, iso-butenyl, 1-pentenyl, 2-pentenyl, 2-methyl-1-butenyl, 3-methyl-1-butenyl, 2-methyl-2-butenyl, 2,2-dicyanovinyl, 2-cyano-2-methylcarboxylvinyl, 2-cyano-2-methylsulfonevinyl, styryl and 4-phenyl-2-butenyl.

Examples of substituted or unsubstituted alkoxy for $R^1$ to $R^{12}$ include straight, branched or circular unsubstituted alkoxy having 1 to 15 carbon atoms such as methoxy, ethoxy, n-propoxy, isopropoxy, n-butoxy, isobutoxy, tert-butoxy, sec-butoxy, n-pentyloxy, isopentyloxy, tert-pentyloxy, sec-pentyloxy, cyclopentyloxy, n-hexyloxy, 1-methylpentyloxy, 2-methylpentyloxy, 3-methylpentyloxy, 4-methylpentyloxy, 1,1-dimethylbutoxy, 1,2-dimethylbutoxy, 1,3-dimethylbutoxy, 2,3-dimethylbutoxy, 1,1,2-trimethylpropoxy, 1,2,2-trimethylpropoxy, 1-ethylbutoxy, 2-ethylbutoxy, 1-ethyl-2-methylpropoxy, cyclohexyloxy, methylcyclopentyloxy, n-heptyloxy, 1-methylhexyloxy, 2-methylhexyloxy, 3-methylhexyloxy, 4-methylhexyloxy, 5-methylhexyloxy, 1,1-dimethylpentyloxy, 1,2-dimethylpentyloxy, 1,3-dimethylpentyloxy, 1,4-dimethylpentyloxy, 2,2-dimethylpentyloxy, 2,3-dimethylpentyloxy, 2,4-dimethylpentyloxy, 3,3-dimethylpentyloxy, 3,4-dimethylpentyloxy, 1-ethylpentyloxy, 2-ethylpentyloxy, 3-ethylpentyloxy, 1,1,2-trimethylbutoxy, 1,1,3-trimethylbutoxy, 1,2,3-trimethylbutoxy, 1,2,2-trimethylbutoxy, 1,3,3-trimethylbutoxy, 2,3,3-trimethylbutoxy, 1-ethyl-1-methylbutoxy, 1-ethyl-2-methylbutoxy, 1-ethyl-3-methylbutoxy, 2-ethyl-1-methylbutoxy, 2-ethyl-3-methylbutoxy, 1-n-propylbutoxy, 1-isopropylbutoxy, 1-isopropyl-2-methylpropoxy, methylcyclohexyloxy, n-octyloxy, 1-methylheptyloxy, 2-methylheptyloxy, 3-methylheptyloxy, 4-methylheptyloxy, 5-methylheptyloxy, 6-methylheptyloxy, 1,1-dimethylhexyloxy, 1,2-dimethylhexyloxy, 1,3-dimethylhexyloxy, 1,4-dimethylhexyloxy, 1,5-dimethylhexyloxy, 2,2-dimethylhexyloxy, 2,3-diethylhexyloxy, 2,4-dimethylhexyloxy, 2,5-dimethylhexyloxy, 3,3-dimethylhexyloxy, 3,4-dimethylhexyloxy, 3,5-dimethylhexyloxy, 4,4-dimethylhexyloxy, 4,5-dimethylhexyloxy, 1-ethylhexyloxy, 2-ethylhexyloxy, 3-ethylhexyloxy, 4-ethylhexyloxy, 1-n-propylpentyloxy, 2-n-propylpentyloxy, 1-isopropylpentyloxy, 2-isopropylpentyloxy, 1-ethyl-1-methylpentyloxy, 1-ethyl-2-methylpentyloxy, 1-ethyl-3-methylpentyloxy, 1-ethyl-4-methylpentyloxy, 2-ethyl-1-methylpentyloxy, 2-ethyl-2-methylpentyloxy, 2-ethyl-3-methylpentyloxy, 2-ethyl-4-methylpentyloxy, 3-ethyl-1-methylpentyloxy, 3-ethyl-2-methylpentyloxy, 3-ethyl-3-methylpentyloxy, 3-ethyl-4-methylpentyloxy, 1,1,2-trimethylpentyloxy, 1,1,3-trimethylpentyloxy, 1,1,4-trimethylpentyloxy, 1,2,2-trimethylpentyloxy, 1,2,3-trimethylpentyloxy, 1,2,4-trimethylpentyloxy, 1,3,4-trimethylpentyloxy, 2,2,3-trimethylpentyloxy, 2,2,4-trimethylpentyloxy, 2,3,4-trimethylpentyloxy, 1,3,3-trimethylpentyloxy, 2,3,3-trimethylpentyloxy, 3,3,4-trimethylpentyloxy, 1,4,4-trimethylpentyloxy, 2,4,4-trimethylpentyloxy, 3,4,4-trimethylpentyloxy, 1-n-butylbutoxy, 1-isobutylbutoxy, 1-sec-butylbutoxy, 1-tert-butylbutoxy, 2-tert-butylbutoxy, 1-n-propyl-1-methylbutoxy, 1-n-propyl-2-methylbutoxy, 1-n-propyl-3-methylbutoxy, 1-isopropyl-1-methylbutoxy, 1-isopropyl-2-methylbutoxy, 1-isopropyl-3-methylbutoxy, 1,1-diethylbutoxy, 1,2-diethylbutoxy, 1-ethyl-1,2-dimethylbutoxy, 1-ethyl-1,3-dimethylbutoxy, 1-ethyl-2,3-dimethylbutoxy, 2-ethyl-1,1-dimethylbutoxy, 2-ethyl-1,2-dimethylbutoxy, 2-ethyl-1,3-dimethylbutoxy, 2-ethyl-2,3-dimethylbutoxy, 1,1,3,3-tetramethylbutoxy, 1,2-dimethylcyclohexyloxy, 1,3-dimethylcyclohexyloxy, 1,4-dimethylcyclohexyloxy, ethylcyclohexyloxy, n-nonyloxy, 3,5,5-trimethylhexyloxy, n-decyloxy, n-undecyloxy, n-dodecyloxy, 1-adamantyloxy and n-pentadecyloxy;

alkoxy-alkoxy having 2 to 15 carbon atoms such as methoxymethoxy, methoxyethoxy, ethoxyethoxy, n-propoxyethoxy, isopropoxyethoxy, n-butoxyethoxy, isobutoxyethoxy, tert-butoxyethoxy, sec-butoxyethoxy, n-pentyloxyethoxy, isopentyloxyethoxy, tert-pentyloxyethoxy, sec-pentyloxyethoxy, cyclopentyloxyethoxy, n-hexyloxyethoxy, ethylcyclohexyloxyethoxy, n-nonyloxyethoxy, (3,5,5-trimethylhexyloxy)ethoxy, (3,5,5-trimethylhexyloxy)butoxy, n-decyloxyethoxy, n-undecyloxyethoxy, n-dodecyloxyethoxy, 3-methoxypropoxy, 3-ethoxypropoxy, 3-(n-propoxy)propoxy, 2-isopropoxypropoxy, 2-methoxybutoxy, 2-ethoxybutoxy, 2-(n-propoxy)butoxy, 4-isopropoxybutoxy, decalyloxyethoxy and adamantyloxyethoxy;

straight, branched or circular alkoxyalkoxy-alkoxy having 3 to 15 carbon atoms such as methoxymethoxymethoxy, ethoxymethoxymethoxy, propoxymethoxymethoxy, butoxymethoxymethoxy, methoxyethoxymethoxy, ethoxyethoxymethoxy, propoxyethoxymethoxy, butoxyethoxymethoxy, methoxypropoxymethoxy, ethoxypropoxymethoxy, propoxypropoxymethoxy, butoxypropoxymethoxy, methoxybutoxymethoxy, ethoxybutoxymethoxy, propoxybutoxymethoxy, butoxybutoxymethoxy, methoxymethoxyethoxy, ethoxymethoxyethoxy, propoxymethoxyethoxy, butoxymethoxyethoxy, methoxyethoxyethoxy, ethoxyethoxyethoxy, propoxyethoxyethoxy, butoxyethoxyethoxy, methoxypropoxyethoxy, ethoxypropoxyethoxy, propoxypropoxyethoxy, butoxypropoxyethoxy, methoxybutoxyethoxy, ethoxybutoxyethoxy, propoxybutoxyethoxy, butoxybutoxyethoxy, methoxymethoxypropoxy, ethoxymethoxypropoxy, propoxymethoxypropoxy, butoxymethoxypropoxy, methoxyethoxypropoxy, ethoxyethoxypropoxy, propoxyethoxypropoxy, butoxyethoxypropoxy, methoxypropoxypropoxy, ethoxypropoxypropoxy, propoxypropoxypropoxy, butoxypropoxypropoxy, methoxybutoxypropoxy, ethoxybutoxypropoxy, propoxybutoxypropoxy, butoxybutoxypropoxy, methoxymethoxybutoxy, ethoxymethoxybutoxy, propoxymethoxybutoxy, butoxymethoxybutoxy, methoxyethoxybutoxy, ethoxyethoxybutoxy, propoxyethoxybutoxy, butoxyethoxybutoxy, methoxypropoxybutoxy, ethoxypropoxybutoxy, propoxypropoxybutoxy, butoxypropokybutoxy, methoxybutoxybutoxy, ethoxybutoxybutoxy, propoxybutoxybutoxy, butoxybutoxybutoxy, (4-ethylcyclohexyloxy)ethoxyethoxy, (2-ethyl-1-hexyloxy)ethoxypropoxy and [4-(3,5,5-trimethylhexyloxy)butoxy]ethoxy;

alkoxycarbonyl-alkoxy having 3 to 10 carbon atoms such as methoxycarbonylmethoxy, ethoxycarbonylmethoxy, n-propoxycarbonylmethoxy, isopropoxycarbonylmethoxy and (4'-ethylcyclohexyloxy) carbonylmethoxy;

acyl-alkoxy having 3 to 10 carbon atoms such as acetylmethoxy, ethylcarbonylmethoxy, octylcarbonylmethoxy and phenacyloxy;

acyloxy-alkoxy having 3 to 10 carbon atoms such as acetyloxymethoxy, acetyloxyethoxy, acetyloxyhexyloxy and butanoyloxycyclohexyloxy;

alkylamino-alkoxy having 2 to 10 carbon atoms such as methylaminomethoxy, 2-methylaminoethoxy, 2-(2-methylaminoethoxy)ethoxy, 4-methylaminobutoxy, 1-methylaminopropan-2-yloxy, 3-methylaminopropoxy, 2-methylamino-2-methylpropoxy, 2-ethylaminoethoxy, 2-(2-ethylaminoethoxy)ethoxy, 3-ethylaminopropoxy, 1-ethylaminopropoxy, 2-isopropylaminoethoxy, 2-(n-butylamino)ethoxy, 3-(n-hexylamino)propoxy and 4-(cyclohexylamino)butyloxy;

alkylaminoalkoxy-alkoxy having 3 to 10 carbon atoms such as methylaminomethoxymethoxy, methylaminoethoxyethoxy, methylaminoethoxypropoxy, ethylaminoethoxypropoxy and 4-(2'-isobutylaminopropoxy)butoxy;

dialkylamino-alkoxy having 3 to 15 carbon atoms such as dimethylaminomethoxy, 2-dimethylaminoethoxy, 2-(2-dimethylaminoethoxy)ethoxy, 4-dimethylaminobutoxy, 1-dimethylaminopropan-2-yloxy, 3-dimethylaminopropoxy, 2-dimethylamino-2-methylpropoxy, 2-diethylaminoethoxy, 2-(2-diethylaminoethoxy)ethoxy, 3-diethylaminopropoxy, 1-diethylaminopropoxy, 2-diisopropylaminoethoxy, 2-(di-n-butylamino)ethoxy, 2-piperidylethoxy and 3-(di-n-hexylamino,)propoxy;

dialkylaminoalkoxy-alkoxy having 4 to 15 carbon atoms such as dimethylaminomethoxymethoxy, dimethylaminoethoxyethoxy, dimethylaminoethoxypropoxy, diethylaminoethoxypropoxy and 4-(2'-diisobutylaminopropoxy)butoxy; and alkylthio-alkoxy having 2 to 15 carbon atoms such as methylthiomethoxy, 2-methylthioethoxy, 2-ethylthioethoxy, 2-n-propylthioethoxy, 2-isopropylthioethoxy, 2-n-butylthioethoxy, 2-isobutylthioethoxy and (3,5,5-trimethylhexylthio) hexyloxy. Preferable examples include alkoxy having 1 to 10 carbon atoms such as methoxy, ethoxy, n-propoxy, iso-propoxy, n-butoxy, iso-butoxy, sec-butoxy, t-butoxy, n-pentoxy, iso-pentoxy, neopentoxy, 2-methylbutoxy, 2-ethylhexyloxy, 3,5,5-trimethylhexyloxy, decalyloxy, methoxyethoxy, ethoxyethoxy, methoxyethoxyethoxy and ethoxyethoxyethoxy.

Examples of substituted or unsubstituted aralkyloxy for $R^1$ to $R^{12}$ include aralkyloxy optionally substituted as described above for alkyl; preferably, aralkyloxy having 7 to 15 carbon atoms such as benzyloxy, nitrobenzyloxy, cyanobenzyloxy, hydroxybenzyloxy, methylbenzyloxy, trifluoromethylbenzyloxy, naphthylmethoxy, nitronaphthylmethoxy, cyanonaphthylmethoxy, hydroxynaphthylmethoxy, methylnaphthylmethoxy, trifluoromethylnaphthylmethoxy and fluoren-9-ylethoxy.

Examples of substituted or unsubstituted aryloxy for $R^1$ to $R^{12}$ include aryloxy optionally substituted as described above for alkyl; preferably, aryloxy having 6 to 18 carbon atoms such as phenoxy, 2-methylphenoxy, 4-methylphenoxy, 4-t-butylphenoxy, 2-methoxyphenoxy, 4-iso-propylphenoxy, naphthoxy, ferrocenyloxy, cobaltocenyloxy, nickelocenyloxy, octamethylferrocenyloxy, octamethylcobaltocenyloxy and octamethylnickelocenyloxy.

Examples of substituted or unsubstituted alkenyloxy for $R^1$ to $R^{12}$ include alkenyloxy optionally substituted as described above for alkyl; preferably, alkenyloxy having 2 to 10 carbon atoms such as vinyloxy, propenyloxy, 1-butenyloxy, iso-butenyloxy, 1-pentenyloxy, 2-pentenyloxy, 2-methyl-1-butenyloxy, 3-methyl-1-butenyloxy, 2-methyl-2-butenyloxy, cyclopentadienyloxy, 2,2-dicyanovinyloxy, 2-cyano-2-methylcarboxylvinyloxy, 2-cyano-2-methylsulfonevinyloxy, styryloxy, 4-phenyl-2-butenyloxy and cinnamyloxy.

Examples of substituted or unsubstituted alkylthio for $R^1$ to $R^{12}$ include alkylthio optionally substituted as described above for alkyl; preferably, alkylthio having 1 to 10 carbon atoms such as methylthio, ethylthio, n-propylthio, iso-propylthio, n-butylthio, iso-butylthio, sec-butylthio, t-butylthio, n-pentylthio, iso-pentylthio, neopentylthio, 2-methylbutylthio, methylcarboxylethylthio, 2-ethylhexylthio, 3,5,5-trimethylhexylthio and decalylthio.

Examples of substituted or unsubstituted aralkylthio for $R^1$ to $R^{12}$ include aralkylthio optionally substituted as described above for alkyl; preferably, aralkylthio having 7 to 12 carbon atoms such as benzylthio, nitrobenzylthio, cyanobenzylthio, hydroxybenzylthio, methylbenzylthio, trifluoromethylbenzylthio, naphthylmethylthio, nitronaphthylmethylthio, cyanonaphthylmethylthio, hydroxynaphthylmethylthio, methylnaphthylmethylthio, trifluoromethylnaphthylmethylthio and fluoren-9-ylethylthio.

Examples of substituted or unsubstituted arylthio for $R^1$ to $R^{12}$ include arylthio optionally substituted as described above for alkyl; preferably, arylthio having 6 to 10 carbon atoms such as phenylthio, 4-methylphenylthio, 2-methoxyphenylthio, 4-t-butylphenylthio, naphthylthio, ferrocenylthio, cobaltocenylthio, nickelocenylthio, octamethylferrocenylthio, octamethylcobaltocenylthio and octamethylnickelocenylthio.

Examples of substituted or unsubstituted alkenylthio for $R^1$ to $R^{12}$ include alkenylthio optionally substituted as described above for alkyl; preferably, alkenylthio having 2 to 10 carbon atoms such as vinylthio, allylthio, butenylthio, hexanedienylthio, cyclopentadienylthio, styrylthio, cyclohexenylthio and decenylthio.

Examples of substituted or unsubstituted acyl for $R^1$ to $R^{12}$ include acyl optionally substituted as described above for alkyl; preferably, acyl having 1 to 15 carbon atoms such as formyl, methylcarbonyl, ethylcarbonyl, n-propylcarbonyl, iso-propylcarbonyl, n-butylcarbonyl, iso-butylcarbonyl, sec-butylcarbonyl, t-butylcarbonyl, n-pentylcarbonyl, iso-pentylcarbonyl, neopentylcarbonyl, 2-methylbutylcarbonyl, benzoyl, methylbenzoyl, ethylbenzoyl, tolylcarbonyl, propylbenzoyl, 4-t-butylbenzoyl, nitrobenzylcarbonyl, 3-butoxy-2-naphthoyl, cinnamoyl, ferrocenecarbonyl and 1-methylferrocene-1'-carbonyl.

Examples of substituted or unsubstituted acyloxy for $R^1$ to $R^{12}$ include acyloxy optionally substituted as described above for alkyl; preferably, acyloxy having 2 to 16 carbon atoms such as formyloxy, methylcarbonyloxy, ethylcarbonyloxy, n-propylcarbonyloxy, iso-propylcarbonyloxy, n-butylcarbonyloxy, iso-butylcarbonyloxy, sec-butylcarbonyloxy, t-butylcarbonyloxy, n-pentylcarbonyloxy, iso-pentylcarbonyloxy, neopentylcarbonyloxy, 2-methylbutylcarbonyloxy, benzoyloxy, methylbenzoyloxy, ethylbenzoyloxy, tolylcarbonyloxy, propylbenzoyloxy, 4-t-butylbenzoyloxy, nitrobenzylcarbonyloxy, 3-butoxy-2-naphthoyloxy, cinnamoyloxy, ferrocenecarbonyloxy, 1-methylferrocene-1'-carbonyloxy, cobaltocenecarbonyloxy and nickelocenecarbonyloxy.

Examples of mono-substituted amino for $R^1$ to $R^{12}$ include mono-substituted amino having a substituent which may be optionally substituted as described above for alkyl; preferably, mono-substituted amino including monoalkylamino having 1 to 10 carbon atoms such as methylamino, ethylamino, propylamino, butylamino, pentylamino, hexylamino, heptylamino, octylamino, (2-ethylhexyl)amino, cyclohexylamino, (3,5,5-trimethylhexyl)amino, nonylamino and decylamino;

monoaralkylamino having 7 to 10 carbon atoms such as benzylamino, phenetylamino, (3-phenylpropyl)amino, (4-ethylbenzyl)amino, (4-isopropylbenzyl)amino, (4-methylbenzyl)amino, (4-ethylbenzyl)amino, (4-allylbenzyl)amino, [4-(2-cyanoethyl)benzyl]amino and [4-(2-acetoxyethyl)benzyl]amino;

monoarylamino having 6 to 10 carbon atoms such as anilino, naphthylamino, toluidino, xylidino, ethylanilino, isopropylanilino, methoxyanilino, ethoxyanilino, chloroanilino, acetylanilino, methoxycarbonylanilino, ethoxycarbonylanilino, propoxycarbonylanilino, 4-methylanilino, 4-ethylanilino, ferrocenylamino, cobaltocenylamino, nickelocenylamino, zirconocenylamino, octamethylferrocenylamino, octamethylcobaltocenylamino, octamethylnickelocenylamino and octamethylzirconocenylamino;

monoalkenylamino having 2 to 10 carbon atoms such as vinylamino, allylamino, butenylamino, pentenylamino, hexenylamino, cyclohexenylamino, cyclopentadienylamino, octadienylamino and adamantenylamino; and monoacylamino having 1 to 16 carbon atoms such as formylamino, methylcarbonylamino, ethylcarbonylamino, n-propylcarbonylamino, iso-propylcarbonylamino, n-butylcarbonylamino, iso-butylcarbonylamino, sec-butylcarbonylamino, t-butylcarbonylamino, n-pentylcarbonylamino, iso-pentylcarbonylamino, neopentylcarbonylamino, 2-methylbutylcarbonylamino, benzoylamino, methylbenzoylamino, ethylbenzoylamino, tolylcarbonylamino, propylbenzoylamino, 4-t-butylbenzoylamino, nitrobenzylcarbonylamino, 3-butoxy-2-naphthoylamino, cinnamoylamino, ferrocenecarbonylamino, 1-methylferrocene-1'-carbonylamino, cobaltocenecarbonylamino and nickelocenecarbonylamino.

Examples of di-substituted amino for $R^1$ to $R^{12}$ include di-substituted amino having two substituents which may be optionally substituted as described above for alkyl; preferably, dialkylamino having 2 to 16 carbons such as dimethylamino, diethylamino, methylethylamino, dipropylamino, dibutylamino, di-n-hexylamino, dicyclohexylamino, dioctylamino, bis(methoxyethyl)amino, bis(ethoxyethyl)amino, bis(propoxyethyl)amino, bis(butoxyethyl)amino, di(acetyloxyethyl)amino, di(hydroxyethyl)amino, N-ethyl-N-(2-cyanoethyl)amino and di(propionyloxyethyl)amino;

diaralkylamino having 14 to 20 carbon atoms such as dibenzylamino, diphenetylamino, bis(4-ethylbenzyl)amino and bis(4-isopropylbenzyl)amino;

diarylamino having 12 to 14 carbon atoms such as diphenylamino, ditolylamino and N-phenyl-N-tolylamino;

dialkenylamino having 4 to 12 carbon atoms such as divinylamino, diallylamino, dibutenylamino, dipentenylamino, dihexenylamino, bis(cyclopentadienyl)amino and N-vinyl-N-allylamino;

diacylamino having 2 to 30 carbon atoms such as diformylamino, di(methylcarbonyl)amino, di(ethylcarbonyl)amino, di(n-propylcarbonyl)amino, di(iso-propylcarbonyl)amino, di(n-butylcarbonyl)amino, di(iso-butylcarbonyl)amino, di(sec-butylcarbonyl)amino, di(t-butylcarbonyl)amino, di(n-pentylcarbonyl)amino, di(iso-pentylcarbonyl)amino, di(neopentylcarbonyl)amino, di(2-methylbutylcarbonyl)amino, di(benzoyl)amino, di(methylbenzoyl)amino, di(ethylbenzoyl)amino, di(tolylcarbonyl)amino, di(propylbenzoyl)amino, di(4-t-butylbenzoyl)amino, di(nitrobenzylcarbonyl)amino, di(3-butoxy-2-naphthoyl)amino, di(cinnamoyl)amino and succinimino; and di-substituted amino having 3 to 24 carbon atoms and having two substituents selected from substituted or unsubstituted alkyl, aralkyl, aryl and alkenyl groups, such as N-phenyl-N-allylamino, N-(2-acetyloxyethyl)-N-ethylamino, N-tolyl-N-methylamino, N-vinyl-N-methylamino, N-benzyl-N-allylamino, N-methyl-ferrocenylamino, N-ethyl-cobaltocenylamino, N-butyl-nickelocenylamino, N-hexyl-octamethylferrocenylamino, N-methyl-octamethylcobaltocenylamino and N-methyl-octamethylnickelocenylamino.

Examples of substituted or unsubstituted alkoxycarbonyl for $R^1$ to $R^{12}$ include alkoxycarbonyl optionally substituted as described above for alkyl; preferably, alkoxycarbonyl having 2 to 11 carbon atoms such as methoxycarbonyl, ethoxycarbonyl, n-propoxycarbonyl, iso-propoxycarbonyl, n-butoxycarbonyl, iso-butoxycarbonyl, sec-butoxycarbonyl, t-butoxycarbonyl, n-pentoxycarbonyl, iso-pentoxycarbonyl, neopentoxycarbonyl, 2-pentoxycarbonyl, 2-ethylhexyloxycarbonyl, 3,5,5-trimethylhexyloxycarbonyl, decalyloxycarbonyl, cyclohexyloxycarbonyl, chloroethoxycarbonyl, hydroxymethoxycarbonyl and hydroxyethoxycarbonyl;

alkoxycarbonyl having 3 to 11 carbon atoms, which is substituted by an alkoxy group, such as methoxymethoxycarbonyl, methoxyethoxycarbonyl, ethoxyethoxycarbonyl, propoxyethoxycarbonyl, butoxyethoxycarbonyl, pentoxyethoxycarbonyl, hexyloxyethoxycarbonyl, butoxybutoxycarbonyl, hexyloxybutoxycarbonyl, hydroxymethoxymethoxycarbonyl and hydroxyethoxyethoxycarbonyl;

alkoxycarbonyl having 4 to 11 carbon atoms, which is substituted by an alkoxyalkoxy group, such as methoxymethoxymethoxycarbonyl, methoxyethoxyethoxycarbonyl, ethoxyethoxyethoxycarbonyl, propoxyethoxyethoxycarbonyl, butoxyethoxyethoxycarbonyl, pentoxyethoxyethoxycarbonyl and hexyloxyethoxyethoxycarbonyl;

metallocenyl-substituted alkoxycarbonyl having 11 to 20 carbon atoms such as ferrocenylmethoxycarbonyl, ferrocenylethoxycarbonyl, ferrocenylpropoxycarbonyl, ferrocenylbutoxycarbonyl, ferrocenylpentyloxycarbonyl, ferrocenylhexyloxycarbonyl, ferrocenylheptyloxycarbonyl, ferrocenyloctyloxycarbonyl, ferrocenylnonyloxycarbonyl, ferrocenyldecyloxycarbonyl, cobaltocenylmethoxycarbonyl, cobaltocenylethoxycarbonyl, cobaltocenylpropoxycarbonyl, cobaltocenylbutoxycarbonyl, cobaltocenylpentyloxycarbonyl, cobaltodenylhexyloxycarbonyl, cobaltocenylheptyloxycarbonyl, cobaltocenyloctyloxycarbonyl, cobaltocenylnonyloxycarbonyl, cobaltocenyldecyloxycarbonyl, nickelocenylmethoxycarbonyl, nickelocenylethoxycarbonyl, nickelocenylpropoxycarbonyl, nickelocenylbutoxycarbonyl, nickelocenylpentyloxycarbonyl, nickelocenylhexyloxycarbonyl, nickelocenylheptyloxycarbonyl, nickelocenyloctyloxycarbonyl, nickelocenylnonyloxycarbonyl, nickelocenyldecyloxycarbonyl, dichlorotitanocenylmethoxycarbonyl, trichlorotitaniumcyclopentadienylmethoxycarbonyl, bis(trifluoromethanesulfonate)titanocenemethoxycarbonyl, dichlorozirconocenylmethoxycarbonyl, dimethylzirconocenylmethoxycarbonyl, diethoxyzirconocenylmethoxycarbonyl, bis(cyclopentadienyl)chromiummethoxycarbonyl, bis(cyclopentadienyl)dichlorohafniummethoxycarbonyl, bis(cyclopentadienyl)dichloroniobiummethoxycarbonyl, bis(cyclopentadienyl)niobiummethoxycarbonyl, bis(cyclopentadienyl)vanadiummethoxycarbonyl, bis(cyclopentadienyl)dichlorovanadiummethoxycarbonyl and bis(cyclopentadienyl)osmiummethoxycarbonyl.

Examples of substituted or unsubstituted aralkyloxycarbonyl for $R^1$ to $R^{12}$ include aralkyloxycarbonyl optionally substituted as described above foralkyl; preferably, aralkyloxycarbonyl having 8 to 16 carbon atoms such as benzyloxycarbonyl, nitrobenzyloxycarbonyl, cyanobenzyloxycarbonyl, hydroxybenzyloxycarbonyl, methylbenzyloxycarbonyl, trifluoromethylbenzyloxycarbonyl, naphthylmethoxycarbonyl, nitronaphthylmethoxycarbonyl, cyanonaphthylmethoxycarbonyl, hydroxynaphthylmethoxycarbonyl, methylnaphthylmethoxycarbonyl, trifluoromethylnaphthylmethoxycarbonyl and fluoren-9-ylethoxycarbonyl.

Examples of substituted or unsubstituted aryloxycarbonyl for $R^1$ to $R^{12}$ include aryloxycarbonyl optionally substituted as described above for aryl; preferably, aryloxycarbonyl having 7 to 11 carbon atoms such as phenoxycarbonyl, 2-methylphenoxycarbonyl, 4-methylphenoxycarbonyl, 4-t-butylphenoxycarbonyl, 2-methoxyphenoxycarbonyl, 4-isopropylphenoxycarbonyl, naphthoxycarbonyl, ferrocenyloxycarbonyl, cobaltocenyloxycarbonyl, nickelocenyloxycarbonyl, zirconocenyloxycarbonyl, octamethylferrocenyloxycarbonyl, octamethylcobaltocenyloxycarbonyl, octamethylnickelocenyloxycarbonyl and octamethylzirconocenyloxycarbonyl.

Examples of substituted or unsubstituted alkenyloxycarbonyl for $R^1$ to $R^{12}$ include alkenyloxycarbonyl optionally substituted as described above for alkyl; preferably, alkenyloxycarbonyl having 3 to 11 carbon atoms such as vinyloxycarbonyl, propenyloxycarbonyl, 1-butenyloxycarbonyl, iso-butenyloxycarbonyl, 1-pentenyloxycarbonyl, 2-pentenyloxycarbonyl, cyclopentadienyloxycarbonyl, 2-methyl-o-butenyloxycarbonyl, 3-methyl-1-butenyloxycarbonyl, 2-methyl-2-butenyloxycarbonyl, 2,2-dicyanovinyloxycarbonyl, 2-cyano-2-methylcarboxylvinyloxycarbonyl, 2-cyano-2-methylsulfonevinyloxycarbonyl, styryloxycarbonyl and 4-phenyl-2-butenyloxycarbonyl.

Examples of mono-substituted aminocarbonyl for $R^1$ to $R^{12}$ include mono-substituted aminocarbonyl having a substituent which may be optionally substituted as described above for alkyl; preferably, monoalkylaminocarbonyl having 2 to 11 carbon atoms such as methylaminocarbonyl, ethylaminocarbonyl, propylaminocarbonyl, butylaminocarbonyl, pentylaminocarbonyl, hexylaminocarbonyl, heptylaminocarbonyl, octylaminocarbonyl, (2-ethylhexyl)aminocarbonyl, cyclohexylaminocarbonyl, (3,5,5-trimethylhexyl)aminocarbonyl, nonylaminocarbonyl and decylaminocarbonyl;

monoaralkylaminocarbonyl having 8 to 11 carbon atoms such as benzylaminocarbonyl, phenetylaminocarbonyl, (3-phenylpropyl)aminocarbonyl, (4-ethylbenzyl)aminocarbonyl, (4-isopropylbenzyl)aminocarbonyl, (4-methylbenzyl)aminocarbonyl, (4-ethylbenzyl)aminocarbonyl, (4-allylbenzyl)aminocarbonyl, [4-(2-cyanoethyl)benzyl]aminocarbonyl and [4-(2-acetoxyethyl)benzyl]aminocarbonyl;

monoarylaminocarbonyl having 7 to 11 carbon atoms such as anilinocarbonyl, naphthylaminocarbonyl, toluidinocarbonyl, xylidinocarbonyl, ethylanilinocarbonyl, isopropylanilinocarbonyl, methoxyanilinocarbonyl, ethoxyanilinocarbonyl, chloroanilinocarbonyl, acetylanilinocarbonyl, methoxycarbonylanilinocarbonyl, ethoxycarbonylanilinocarbonyl, propoxycarbonylanilinocarbonyl, 4-methylanilinocarbonyl and 4-ethylanilinocarbonyl; and monoalkenylaminocarbonyl having 3 to 11 carbon atoms such as vinylaminocarbonyl, allylaminocarbonyl, butenylaminocarbonyl, pentenylaminocarbonyl, hexenylaminocarbonyl, cyclohexenylaminocarbonyl, octadienylaminocarbonyl and adamantenylaminocarbonyl.

Examples of di-substituted aminocarbonyl for $R^1$ to $R^{12}$ include di-substituted aminocarbonyl having two substituents which may be optionally substituted as described above for alkyl; preferably, dialkylaminocarbonyl having 3 to 17 carbon atoms such as dimethylaminocarbonyl, diethylaminocarbonyl, methylethylaminocarbonyl, dipropylaminocarbonyl, dibutylaminocarbonyl, di-n-hexylaminocarbonyl, dicyclohexylaminocarbonyl, dioctylaminocarbonyl, pyrrolidinocarbonyl, piperidinocarbonyl, morpholinocarbonyl, bis(methoxyethyl)aminocarbonyl, bis(ethoxyethyl)aminocarbonyl, bis(propoxyethyl)aminocarbonyl, bisp(butoxyethyl)aminocarbonyl, di(acetyloxyethyl)aminocarbonyl, di(hydroxyethyl)aminocarbonyl, N-ethyl-N-(2-cyanoethyl)aminocarbonyl and di(propionyloxyethyl)aminocarbonyl;

diaralkylaminocarbonyl having 15 to 21 carbon atoms such as dibenzylaminocarbonyl, diphenetylaminocarbonyl, bis(4-ethylbenzyl)aminocarbonyl and bis(4-isopropylbenzyl)aminocarbonyl;

diarylaminocarbonyl having 13 to 15 carbon atoms such as diphenylaminocarbonyl, ditolylaminocarbonyl and N-phenyl-N-tolylaminocarbonyl;

dialkenylaminocarbonyl having 5 to 13 carbon atoms such as divinylaminocarbonyl, diallylaminocarbonyl, dibutenylaminocarbonyl, dipentenylaminocarbonyl, dihexenylaminocarbonyl and N-vinyl-N-allylaminocarbonyl; and di-substituted aminocarbonyl having 4 to 11 carbon atoms and having two substituents selected from substituted or unsubstituted alkyl, aralkyl, aryl and alkenyl groups, such as N-phenyl-N-allylaminocarbonyl, N-(2-acetyloxyethyl)-N-ethylaminocarbonyl, N-tolyl-N-methylaminocarbonyl, N-vinyl-N-methylaminocarbonyl and N-benzyl-N-allylaminocarbonyl.

Examples of substituted or unsubstituted heteroaryl for $R^1$ to $R^{12}$ include heteroaryl optionally substituted as described above for alkyl; preferably, unsubstituted heteroaryl such as furanyl, pyrrolyl, 3-pyrrolino, pyrazolyl, imidazolyl, oxazolyl, thiazolyl, 1,2,3-oxadiazolyl, 1,2,3-triazolyl, 1,2,4-triazolyl, 1,3,4-thiadiazolyl, pyridinyl, pyridazinyl, pyrimidinyl, pyradinyl, piperadinyl, triazinyl, benzofuranyl, indolyl, thionaphthenyl, benzimidazolyl, benzothiazolyl, benzotriazol-2-yl, benzotriazol-1-yl, purinyl, quinolinyl, isoquinolinyl, coumarinyl, cinnolinyl, quinoxalinyl, dibenzofuranyl, carbazolyl, phenanthronilyl, phenothiazinyl, flavonyl, phthalimidyl and naphthylimidyl;

or heteroaryl substituted with a substituent selected from the followings, i.e., halogen such as fluorine, chlorine, bromine and iodine;

cyano;

alkyl such as methyl, ethyl, propyl, butyl, pentyl, hexyl, heptyl, octyl, decyl, methoxymethyl, ethoxyethyl, ethoxyethyl and trifluoromethyl;

aralkyl such as benzyl and phenetyl;

aryl such as phenyl, tolyl, naphthyl, xylyl, mesyl, chlorophenyl and methoxyphenyl;

alkoxy such as methoxy, ethoxy, propoxy, butoxy, pentoxy, hexyloxy, heptyloxy, octyloxy, nonyloxy, decyloxy, 2-ethylhexyloxy, 3,5,5-trimethylhexyloxy, ferrocenemethoxy, cobaltocenemethoxy and nickelocenemethoxy;

aralkyloxy such as benzyloxy and phenetyloxy;

aryloxysuchasphenoxy, tolyloxy, naphthoxy, xylyloxy, mesityloxy, chlorophenoxy and methoxyphenoxy;

alkenyl such as vinyl, allyl, butenyl, butadienyl, pentenyl, cyclopentadienyl and octenyl;

alkenyloxy such as vinyloxy, allyloxy, butenyloxy, butadienyloxy, pentenyloxy, cyclopentadienyloxy and octenyloxy;

alkylthio such as methylthio, ethylthio, propylthio, butylthio, pentylthio, hexylthio, heptylthio, octylthio, decylthio, methoxymethylthio, ethoxyethylthio, ethoxyethylthio and trifluoromethylthio;

aralkylthio such as benzylthio and phenetylthio;

arylthio such as phenylthio, tolylthio, naphthylthio, xylylthio, mesylthio, chlorophenylthio and methoxyphenylthio;

dialkylamino such as dimethylamino, diethylamino, dipropylamino and dibutylamino;

acyl such as acetyl, propionyl, butanoyl, ferrocenecarbonyl, cobaltocenecarbonyl and nickelocenecarbonyl;

alkoxycarbonyl such as methoxycarbonyl, ethoxycarbonyl, ferrocenemethoxycarbonyl, 1-methylferrocene-1'-ylmethoxycarbonyl, cobaltocenylmethoxycarbonyl and nickelocenylmethoxycarbonyl;

aralkyloxycarbonyl such as benzyloxycarbonyl and phenetyloxycarbonyl;

aryloxycarbonyl such as phenoxycarbonyl, tolyloxycarbonyl, naphthoxycarbonyl, xylyloxycarbonyl, mesyloxycarbonyl, chlorophenoxycarbonyl and methoxyphenoxycarbonyl;

alkenyloxycarbonyl such as vinyloxycarbonyl, allyloxycarbonyl, butenyloxycarbonyl, butadienyloxycarbonyl, cyclopentadienyloxy, pentenyloxycarbonyl and octenyloxycarbonyl;

alkylaminocarbonyl including monoalkylaminocarbonyl having 2 to 10 carbon atoms such as methylaminocarbonyl, ethylaminocarbonyl, propylaminocarbonyl, butylaminocarbonyl, pentylaminocarbonyl, hexylaminocarbonyl, heptylaminocarbonyl, octylaminocarbonyl, nonylaminocarbonyl, 3,5,5-trimethylhexylaminocarbonyl and 2-ethylhexylaminocarbonyl, and dialkylaminocarbonyl having 3 to 20 carbon atoms such as dimethylaminocarbonyl, diethylaminocarbonyl, dipropylaminocarbonyl, dibutylaminocarbonyl, dipentylaminocarbonyl, dihexylaminocarbonyl, diheptylaminocarbonyl, dioctylaminocarbonyl, piperidinocarbonyl, morpholinocarbonyl, 4-methylpiperadinocarbonyl and 4-ethylpiperadinocarbonyl;

heterocycle such as furanyl, pyrrolyl, 3-pyrrolino, pyrrolidino, 1,3-oxoranyl, pyrazolyl, 2-pyrazolinyl, pyrazolidinyl, imidazolyl, oxazolyl, thiazolyl, 1,2,3-oxadiazolyl, 1,2,3-triazolyl, 1,2,4-triazolyl, 1,3,4-thiadiazolyl, 4H-pyranyl, pyridinyl, piperidinyl, dioxanyl, morpholinyl, pyridazinyl, pyrimidinyl, pyradinyl, piperadinyl, triazinyl, benzofuranyl, indolyl, thionaphthenyl, benzimidazolyl, benzothiazolyl, purinyl, quinolinyl, isoquinolinyl, coumarinyl, cinnolinyl, quinoxalinyl, dibenzofuranyl, carbazolyl, phenanthronilyl, phenothiadinyl and flavonyl;

metallocenyl such as ferrocenyl, cobaltocenyl, nickelocenyl, ruthenocenyl, osmocenyl and titanocenyl.

Examples of substituted or unsubstituted heteroaryloxy for $R^1$ to $R^{12}$ include heteroaryloxy optionally substituted as described above for alkyl; preferably, unsubstituted heteroaryloxy such as furanyloxy, pyrrolyloxy, 3-pyrrolinooxy, pyrazolyloxy, imidazolyloxy, oxazolyloxy, thiazolyloxy, 1,2,3-oxadiazolyloxy, 1,2,3-triazolyloxy, 1,2,4-triazolyloxy, 1,3,4-thiadiazolyloxy, pyridinyloxy, pyridazinyloxy, pyrimidinyloxy, pyradinyloxy, piperadinyloxy, triazinyloxy, benzofuranyloxy, indolyloxy, thionaphthenyloxy, benzimidazolyloxy, benzothiazolyloxy, benzotriazol-2-yloxy, benzotriazol-1-yloxy, purinyloxy, quinolinyloxy, isoquinolinyloxy, coumarinyloxy, cinnolinyloxy, quinoxalinyloxy, dibenzofuranyloxy, carbazolyloxy, phenanthronilyloxy, phenothiadinyloxy, flavonyloxy, phthalimidyloxy and naphthylimidyloxy; or heteroaryloxy substituted with a substituent selected from the followings, i.e., halogen such as fluorine, chlorine, bromine and iodine;

cyano;

alkyl such as methyl, ethyl, propyl, butyl, pentyl, hexyl, heptyl, octyl, decyl, methoxymethyl, ethoxyethyl, ethoxyethyl and trifluoromethyl;

aralkyl such as benzyl and phenetyl;

aryl such as phenyl, tolyl, naphthyl, xylyl, mesyl, chlorophenyl and methoxyphenyl;

alkoxy such as methoxy, ethoxy, propoxy, butoxy, pentoxy, hexyloxy, heptyloxy, octyloxy, nonyloxy, decyloxy, 2-ethylhexyloxy, 3,5,5-trimethylhexyloxy, ferrocenemethoxy, cobaltocenemethoxy and nickelocenemethoxy;

aralkyloxy such as benzyloxy and phenetyloxy;

aryloxy such as phenoxy, tolyloxy, naphthoxy, xylyloxy, mesityloxy, chlorophenoxy and methoxyphenoxy;

alkenyl such as vinyl, allyl, butenyl, butadienyl, pentenyl, cyclopentadienyl and octenyl;

alkenyloxy such as vinyloxy, allyloxy, butenyloxy, butadienyloxy, pentenyloxy, cyclopentadienyloxy and octenyloxy;

alkylthio such as methylthio, ethylthio, propylthio, butylthio, pentylthio, hexylthio, heptylthio, octylthio, decylthio, methoxymethylthio, ethoxyethylthio, ethoxyethylthio and trifluoromethylthio;

aralkylthio such as benzylthio and phenetylthio;

arylthio such as phenylthio, tolylthio, naphthylthio, xylylthio, mesylthio, chlorophenylthio and methoxyphenylthio;

dialkylamino such as dimethylamino, diethylamino, dipropylamino and dibutylamino;

acyl such as acetyl, propionyl, butanoyl, ferrocenecarbonyl, cobaltocenecarbonyl and nickelocenecarbonyl;

alkoxycarbonyl such as methoxycarbonyl, ethoxycarbonyl, ferrocenemethoxycarbonyl, 1-methylferrocene-1'-ylmethoxycarbonyl, cobaltocenylmethoxycarbonyl and nickelocenylmethoxycarbonyl;

aralkyloxycarbonyl such as benzyloxycarbonyl and phenetyloxycarbonyl;

aryloxycarbonyl such as phenoxycarbonyl, tolyloxycarbonyl, naphthoxycarbonyl, xylyloxycarbonyl, mesyloxycarbonyl, chlorophenoxycarbonyl and methoxyphenoxycarbonyl;

alkenyloxycarbonyl such as vinyloxycarbonyl, allyloxycarbonyl, butenyloxycarbonyl, butadienyloxycarbonyl, cyclopentadienyloxy, pentenyloxycarbonyl and octenyloxycarbonyl;

alkylaminocarbonyl including monoalkylaminocarbonyl having 2 to 10 carbon atoms such as ethylaminocarbonyl, ethylaminocarbonyl, propylaminocarbonyl, butylaminocarbonyl, pentylaminocarbonyl, hexylaminocarbonyl, heptylaminocarbonyl, octylaminocarbonyl, nonylaminocarbonyl, 3,5,5-trimethylhexylaminocarbonyl and 2-ethylhexylaminocarbonyl; and dialkylaminocarbonyl having 3 to 20 carbon atoms such as dimethylaminocarbonyl, diethylaminocarbonyl, dipropylaminocarbonyl, dibutylaminocarbonyl, dipentylaminocarbonyl, dihexylaminocarbonyl, diheptylaminocarbonyl, dioctylaminocarbonyl, piperidinocarbonyl, morpholinocarbonyl, 4-methylpiperadinocarbonyl and 4-ethylpiperadinocarbonyl;

heterocycle such as furanyl, pyrrolyli 3-pyrrolino, pyrrolidino, 1,3-oxoranyl, pyrazolyl, 2-pyrazolinyl, pyrazolidinyl, imidazolyl, oxazolyl, thiazolyl, 1,2,3-oxadiazolyl, 1,2,3-triazolyl, 1,2,4-triazolyl, 1,3,4-thiadiazolyl, 4H-pyranyl, pyridinyl, piperidinyl, dioxanyl, morpholinyl, pyridazinyl, pyrimidinyl, pyradinyl, piperadinyl, triazinyl, benzofuranyl, indolyl, thionaphthenyl, benzimidazolyl, benzothiazolyl, purinyl, quinolinyl, isoquinolinyl, coumarinyl, cinnolinyl, quinoxalinyl, dibenzofuranyl, carbazolyl, phenanthronilyl, phenothiazinyl and flavonyl;

metallocenyl such as ferrocenyl, cobaltocenyl, nickelocenyl., ruthenocenyl, osmocenyl and titanocenyl.

A linking group via which any combination of $R^1$ to $R^{12}$ forms a ring is an appropriate combination of a heteroatom such as nitrogen, oxygen, sulfur, phosphorous, metal and metalloid with a carbon atom. Examples of a preferable linking group include —O—, —S—, —C(=O)— or optionally substituted methylene, imino and metal. These may be appropriately combined to form a desired ring. A ring formed via a linking group may be straight, planar or three-dimensional. Suitable examples of a structure formed after linkage include aliphatic fused ring such as —CH$_2$—CH$_2$—CH$_2$—CH$_2$—, —CH$_2$(NO$_2$)—CH$_2$—CH$_2$—CH$_2$—, —CH(CH$_3$)—CH$_2$—CH$_2$—CH$_2$— and —CH(Cl)—CH$_2$—CH$_2$—;

aromatic fused ring such as —CH=CH—CH=CH—, —C(NO$_2$)=CH—CH=CH—, —C(CH$_3$)=CH—CH=CH—, —C(CH$_3$)=CH—CH=CH—, —C(CH$_3$)=CH—CH=C(CH$_3$)—, —C(OCH$_3$)=CH—CH=C(OCH$_3$)—, —C(OCH$_2$CH$_2$CH(CH$_3$)—(OCH$_3$))=C(Cl)—C(Cl)=C(OCH$_2$CH$_2$CH(CH$_3$)—(OCH$_3$)—, —C(OCH$_2$CH$_2$CH(CH$_3$)$_2$)=C(Cl)—C(Cl)=C(OCH$_2$CH$_2$CH(CH$_3$)$_2$)—, —CH=C(CH$_3$)—C(CH$_3$)=CH—, —C(Cl)=CH—CH=CH—, —C{OCH[CH(CH$_3$)$_2$]$_2$}=CH—CH=CH—, —C{OCH[CH(CH$_3$)$_2$]$_2$}=C(Br)—CH=CH—, —C{OCH[CH(CH$_3$)$_2$]$_2$}=CH—C(Br)=CH—, —C{OCH[CH(CH$_3$)$_2$]$_2$}=CH—CH=C(Br)—, —C(C$_2$H$_5$)=CH—CH=CH—, —C(C$_2$H$_5$)=CH—CH=C(C$_2$H$_5$)—, —CH=C(C$_2$H$_5$)—C(C$_2$H$_5$)=CH— and —C(Cl)=CH—CH=CH—;

linearly linked heterocycles such as —O—CH$_2$—CH$_2$—O—, —O—CH(CH$_3$)—CH(CH$_3$)—O—, —COO—CH$_2$—CH$_2$—, —COO—CH$_2$—, —CONH—CH$_2$—CH$_2$—, —CONH—CH$_2$—, —CON(CH$_3$)—CH$_2$—CH$_2$— and —CON(CH$_3$)—CH$_2$—; or a metal-complex residue such as:

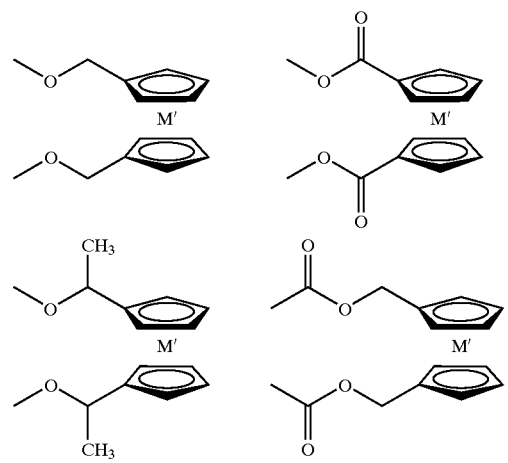

-continued

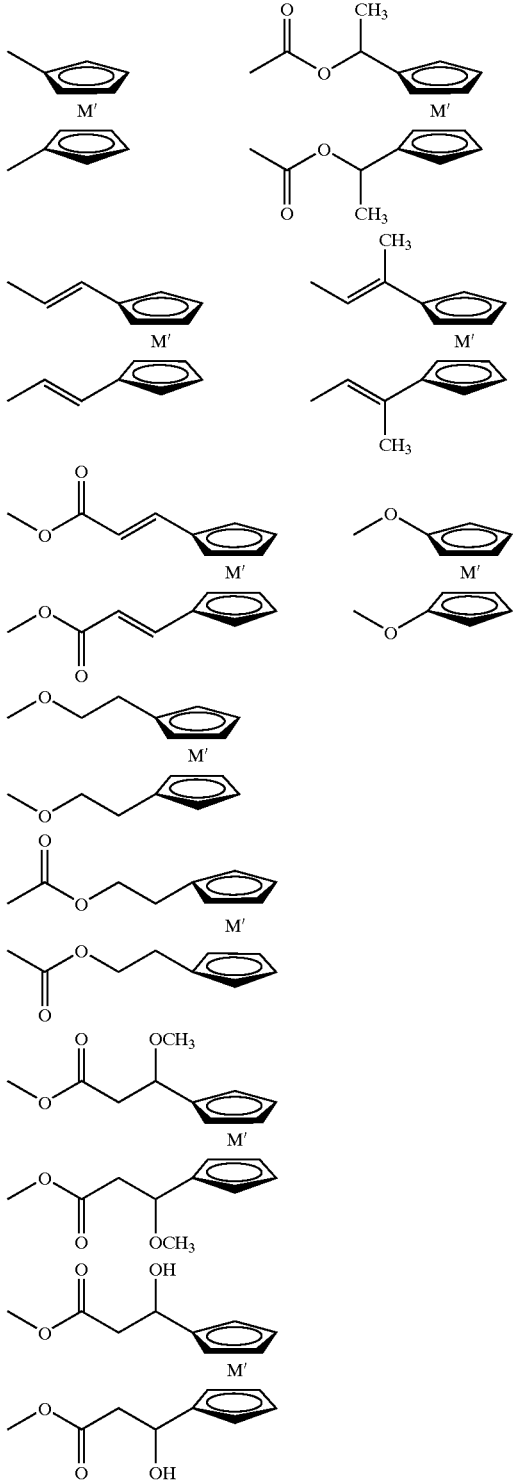

wherein M' represents Fe, Ru, Co, Ni, Os or M"R'$_2$, where M" represents Ti, Zr, Hf, Nb, Mo or V; R' represents CO, F, Cl, Br, I, oralkyl, alkoxy, aryl, aryloxy, aralkyl, aralkyloxy having 1 to 10 carbon atoms and optionally having a substituent as defined above for $R^1$ to $R^{12}$.

Examples of a preferable combination for forming a linkage of any of $R^1$ to $R^{12}$ with an adjacent substituent via a linking group include $R^1$ and $R^2$, $R^3$ and $R^4$, $R^5$ and $R^6$, $R^7$ and $R^8$, $R^9$ and $R^{10}$, $R^{11}$ and $R^{12}$, $R^{12}$ and $R^1$, $R^2$ and $R^3$, $R^4$ and $R^5$, $R^6$ and $R^7$, $R^8$ and $R^9$ as well as $R^{10}$ and $R^{11}$.

A bivalent to tetravalent metal or metalloid atom represented by $M^1$ may be selected from those in Groups IIA to VIIA, VIII and IB to VIIB in the periodic table.

Examples of a bivalent metal atom include bivalent unsubstituted metal such as Cu, Zn, Fe, Co, Ni, Ru, Rh, Pd, Pt, Mn, Sn, Mg, Pb, Hg, Cd, Ba, Ti, Be, Ca, Re and Os; or bivalent metal to which a heterocycle including a substituted or unsubstituted 5-membered nitrogen-containing aromatic compound, six-membered nitrogen-containing aromatic compound or fused nitrogen-containing ring compound; carbon monoxide; or an alcohol coordinates as a ligand.

Examples of a substituted or unsubstituted 5-membered nitrogen-containing aromatic compound coordinating to a bivalent metal atom include pyrrole, 1-methylpyrrole, 3-methylpyrrole, 2,5-dimethylpyrrole, pyrazole, N-methylpyrazole, 3,5-dimethylpyrazole, imidazole, N-methylimidazole, 2-methylimidazole, 4-methylimidazole, 1,2-dimethylimidazole, oxazole, thiazole, 4-methylthiazole, 2,4-dimethylthiazole, 1,2,3-oxadiazole, 1,2,3-triazole, 1,2,4-triazole, 1,3,4-thiadiazole and 2,5-dimethyl-1,3,4-thiadiazole.

Examples of a substituted or unsubstituted 6-membered nitrogen-containing aromatic compound coordinating to a bivalent metal atom include pyridine, 2-methylpyridine, 3-methylpyridine, 4-methylpyridine, 2,3-dimethylpyridine, 2,4-dimethylpyridine, 2,5-dimethylpyridine, 2,6-dimethylpyridine, 3,4-dimethylpyridine, 3,5-dimethylpyridine, 2-chloropyridine, 3-chloropyridine, 2-methoxypyridine, pyridazine, 3-methylpyridazine, pyrimidine, 4-methylpyrimidine, 2-chloropyrimidine, pyradine, 2-methylpyradine, 2,3-dimethylpyradine, 2,5-dimethylpyradine, 2-methoxypyradine and s-triazine.

Examples of a substituted or unsubstituted fused nitrogen-containing compound coordinating to a bivalent metal atom include indole, N-methylindole, 2-methylindole, 3-methylindole, 5-methylindole, 1,2-dimethylindole, 2,3-dimethylindole, 4-chloroindole, 5-chloroindole, 6-chloroindole, 4-methoxyindole, 5-methoxyindole, 6-methoxyindole, benzimidazole, 2-methylbenzimidazole, 5-methylbenzimidazole, 5,6-dimethylbenzimidazole, 5-chlorobenzimidazole, benzothiazole, 2-methylbenzothiazole, 2,5-dimethylbenzothiazole, 2-chlorobenzothiazole, purine, quinoline, 2-methylquinoline, 3-methylquinoline, 4-methylquinoline, 6-methylquinoline, 7-methylquinoline, 8-methylquinoline, 2,4-dimethylquinoline, 2,6-dimethylquinoline, 2-chloroquinoline, 6-chloroquinoline, 8-chloroquinoline, 6-methoxyquinoline, isoquinoline, 1-methylquinoline, quinoxaline, 2-methylquinoxaline, 2,3-dimethylquinoxaline, carbazole, N-methylcarbazole, acridine, 9-methylacridine and phenothiazine.

Examples of a bivalent metal atom include unsubstituted or dicoordinated metal atoms such as Cu, Ni, Co, Rh, Zn, Fe, Fe(CO), Ru(CO), Os(CO), Ru(CO)(C$_2$H$_5$OH), Cu(pyridine)$_2$, Zn(pyridine)$_2$, CO(pyridine)$_2$, Fe(N-methylimidazole) and Co(N-methylimidazole).

Examples of a substituted trivalent metal or metalloid atom represented by M$^1$ include trivalent metal or metalloid atoms in which an unsubstituted trivalent metal or metalloid atom such as Sc, Ti, V, Cr, Mn, Mo, Ag, U, Fe, Co, Ni, Cu, Y, Nb, Ru, Rh, La, Ta, Ir, Au, In, Tl, Bi, Ce, Pr, Nd, Pm, Sm, Eu, Gd, Tb, Dy, Ho, Er, Tm, Yb, Lu, B, As and Sb is bound to a radical selected from halogen, hydroxyl, optionally substituted alkyl, aryl, heteroaryl, alkoxy, aryloxy, heteroaryloxy, alkylthio, arylthio and heteroarylthio for R$^1$ to R$^{12}$; halogen, hydroxyl, optionally substituted alkyl, aryl, heteroaryl, alkoxy, aryloxy, heteroaryloxy, alkylthio, arylthio, heteroarylthio and amino for the amino group; and silyloxy optionally substituted with aryl or alkyl; or from halogen, optionally substituted alkyl, aryl, heteroaryl, alkoxy, aryloxy, heteroaryloxy, alkylthio, arylthio, heteroarylthio and amino like the above substituent, and to which a ligand selected from heterocycles such as substituted or unsubstituted 5-membered nitrogen-containing aromatic compounds, 6-membered nitrogen-containing aromatic compounds and fused nitrogen-containing compounds; carbon monoxide; and an alcohol.

Examples of a silyloxy substituted by alkyl or aryl include trialkylsilyloxy such as trimethylsilyloxy and triethylsilyl; triarylsilyloxy such as triphenylsilyloxy; and alkylarylsilyloxy such as dimethylphenylsilyloxy.

Examples of a trivalent metal atom include monosubstituted trivalent metal atoms such as Al—F, Al—Cl, Al—Br, Al—I, Ga—F, Ga—Cl, Ga—Br, Ga—I, In—F, In—Cl, In—Br, In—I, Ti—F, Ti—Cl, Ti—Br, Ti—I, Al—C$_6$H$_5$, Al—C$_6$H$_4$(CH$_3$), In—C$_6$H$_5$, In—C$_6$H$_4$(CH$_3$), Mn(OH), Mn(OC$_6$H$_5$), Mn[OSi(CH$_3$)$_3$], Fe—Cl, Fe—C$_6$H$_4$F, Fe—C$_6$H$_3$F$_2$, Fe—C$_6$H$_2$F$_3$, Fe—C$_6$HF$_4$, Fe—C$_6$F$_5$, Fe—C$_6$H$_5$, Fe—CH$_3$, Co—CH$_3$, Co—C$_6$H$_5$, Mn—Cl, Fe—Cl(bis(N-methylimidazole)), Fe-(imidazolyloxy) and Ru—Cl.

Preferable examples of a trivalent metalloid atom include monosubstituted trivalent metalloid atoms such as B—F, B—OCH$_3$, B—C$_6$H$_5$, B—C$_6$H$_4$(CH$_3$), B(OH), B(OC$_6$H$_5$) and B[OSi(CH$_3$)$_3$].

Examples of a substituted tetravalent metal or metalloid atom represented by M$^1$ include tetravalent metal or metalloid atoms in which an unsubstituted tetravalent metal or metalloid atom such as Ti, Cr, Sn, Zr, Ge, Mn and Si is bound to a radical selected from halogen, hydroxyl, optionally substituted alkyl, aryl, heteroaryl, alkoxy, aryloxy, heteroaryloxy, alkylthio, arylthio and heteroarylthio for R$^1$ to R$^{12}$; halogen, hydroxyl, optionally substituted alkyl, aryl, heteroaryl, alkoxy, aryloxy, heteroaryloxy, alkylthio, arylthio, heteroarylthio and amino for the amino group; and silyloxy optionally substituted with aryl or alkyl; or from halogen, optionally substituted alkyl, aryl, heteroaryl, alkoxy, aryloxy, heteroaryloxy, alkylthio, arylthio, heteroarylthio and amino like the above substituent, and to which a ligand selected from heterocycles such as substituted or unsubstituted 5-membered nitrogen-containing aromatic compounds, 6-membered nitrogen-containing aromatic compounds and fused nitrogen-containingcompounds; carbon monoxide; and an alcohol.

Preferable examples of a tetravalent metal atom include di-substituted tetravalent metal atoms such as TiF$_2$, TiCl$_2$, TiBr$_2$, TiI$_2$, CrF$_2$, CrCl$_2$, CrBr$_2$, CrI$_2$, SnF$_2$, SnCl$_2$, SnBr$_2$, SnI$_2$, ZrF$_2$, ZrCl$_2$, ZrBr$_2$, ZrI$_2$, GeF$_2$, GeCl$_2$, GeBr$_2$, GeI$_2$, MnF$_2$, MnCl$_2$, MnBr$_2$, MnI$_2$, Ti(OH)$_2$, Cr(OH)$_2$, Sn(OH)$_2$, Zr(OH)$_2$, Ge(OH)$_2$, Mn(OH)$_2$, TiA$_2$, CrA$_2$, SnA$_2$, ZrA$_2$, GeA$_2$, MnA$_2$, Ti(OA)$_2$, Cr(OA)$_2$, Sn(OA)$_2$, Zr(OA)$_2$, Ge(OA)$_2$, Mn(OA)$_2$, Ti(SA)$_2$, Cr(SA)$_2$, Sn(SA)$_2$, Zr(SA)$_2$, Ge(SA)$_2$, Mn(SA)$_2$, Ti(NHA)$_2$, Cr(NHA)$_2$, Sn(NHA)$_2$, Zr(NHA)$_2$, Ge(NHA)$_2$, Mn(NHA)$_2$, Ti(NA$_2$)$_2$, Cr(NA$_2$)$_2$, Sn(NA$_2$)$_2$, Zr(NA$_2$)$_2$, Ge(NA$_2$)$_2$ and Mn(NA$_2$)$_2$ wherein A represents substituted or unsubstituted alkyl, aryl and heteroaryl as described above for alkyl, aryl and heteroaryl in terms of R$^1$ to R$^{12}$.

Examples of a tetravalent metalloid atom include di-substituted tetravalent metalloid atoms such as SiF$_2$, SiCl$_2$, SiBr$_2$, SiI$_2$, Si(OH)$_2$, SiA$_2$, Si(OA)$_2$, Si(SA)$_2$, Si(NHA)$_2$ and Si(NA$_2$)$_2$ wherein A is as defined above.

Examples of an oxymetal atom represented by M$^1$ include VO, MnO, TiO and OsO$_2$.

Preferable examples of M$^1$ include Cu. Ni, Co, Rh, Zn, Fe, MnCl, CoCl, FeCl, Fe(A), Fe(OA), Co(A), Co(OA), Cu(pyridine)$_2$, Zn(pyridine)$_2$, Co(pyridine)$_2$, VO, TiO, TiA$_2$, SiA$_2$, SnA$_2$, RuA$_2$, RhA$_2$, GeA$_2$, Si(OA)$_2$, Sn(OA)$_2$, Ge(OA)$_2$, Si(SA)$_2$, Sn(SA)$_2$ and Ge(SA)$_2$ wherein A is as defined above.

A preferable compound represented by general formula (1) of this invention is a compound represented by general formula (3):

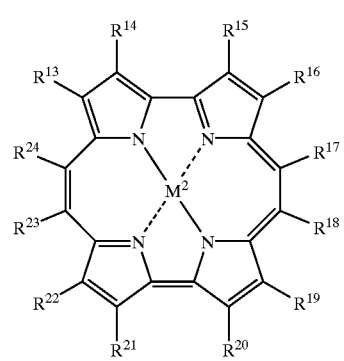

(3)

wherein R$^{13}$ to R$^{24}$ independently represent hydrogen, halogen, nitro, cyano, hydroxyl, amino, carboxyl, mercapto, substituted or unsubstituted alkyl, aralkyl, aryl, alkenyl, alkoxy, aralkyloxy, aryloxy, alkenyloxy, alkylthio, aralkylthio, arylthio, alkenylthio, acyl, acyloxy, mono-substituted amino, di-substituted amino, alkoxycarbonyl, aralkyloxycarbonyl, aryloxycarbonyl, alkenyloxycarbonyl, mono-substituted aminocarbonyl, di-substitutedaminocarbonyl, heteroaryl or heteroaryloxy; each of R$^{13}$ to R$^{24}$ together with an adjacent substituent may form a ring through a linking group; M$^2$ is a bivalent to tetravalent metal atom having a substituent selected from the group consisting of alkyl, aryl and heteroaryloxy group and/or a ligand selected from the group consisting of a carbon monoxide and an alcohol.

Examples of $R^{13}$ to $R^{24}$ in the compound represented by general formula (3) of this invention include hydrogen; halogen such as fluorine, chlorine, bromine and iodine; nitro; cyano; hydroxyl; amino; carboxyl; and mercapto.

Examples of substituted or unsubstituted alkyl, aralkyl, aryl, alkenyl, alkoxy, aralkyloxy, aryloxy, alkenyloxy, alkylthio, aralkylthio, arylthio, alkenylthio, acyl, acyloxy, mono-substituted amino, di-substituted amino, alkoxycarbonyl, aralkyloxycarbonyl, aryloxycarbonyl, alkenyloxycarbonyl, mono-substituted aminocarbonyl, di-substituted aminocarbonyl, heteroaryl or heteroaryloxy for $R^{13}$ to $R^{24}$ may be alkyl, aralkyl, aryl, alkenyl, alkoxy, aralkyloxy, aryloxy, alkenyloxy, alkylthio, aralkylthio, arylthio, alkenylthio, acyl, acyloxy, mono-substituted amino, di-substituted amino, alkoxycarbonyl, aralkyloxycarbonyl, aryloxycarbonyl, alkenyloxycarbonyl, mono-substituted aminocarbonyl, di-substituted aminocarbonyl, heteroaryl or heteroaryloxy for $R^1$ to $R^{12}$.

A linking group via which any combination of $R^{13}$ to $R^{24}$ forms a ring may be as defined above for $R^1$ to $R^{12}$.

A bivalent to tetravalent metal or metalloid atom having a substituent and/or a ligand represented by $M^2$ may be bivalent to tetravalent metal atoms having a substituent selected from alkyl, aryl and heteroaryloxy for $M^1$ and/or a ligand selected from carbon monoxide and an alcohol.

A compound represented by general formula (1) used in this invention may be, for example, prepared by, but not limited to, a process described in Angew. Chem. Int. Ed. Engl. 26, 928–931 (1987), J. Phys. Chem., 98, 11885–11891 (1994). It may be typically prepared by the following reaction.

A porphycene represented by general formula (2) or (3) may be prepared as follows. A compound represented by formula (8) and/or formula (9) is reacted with a metal and/or a metal salt such as zinc and copper (I) chloride; an amine compound such as pyridine; a low-valent titanium generated from titanium tetrachloride; or a titanium compound such as titanium trichloride as appropriate in an ethereal solvent such as anhydrous tetrahydrofuran to give a compound of this invention represented by general formula (10), a compound represented by formula (2) where $M^1$ is two hydrogens.

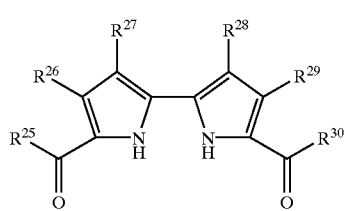

(8)

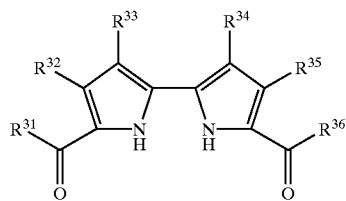

(9)

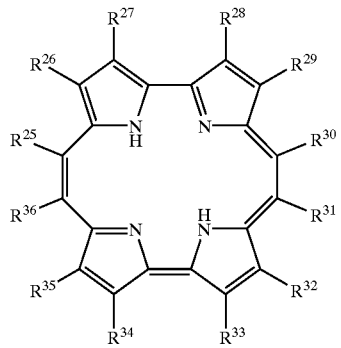

(10)

Wherein $R^{25}$ to $R^{36}$ represent radicals as defined for $R^1$ to $R^{12}$ in formula (2).

The product may be reacted with an acetate, sulfate, nitrate, halide or carbonyl compound of a metal or metalloid in the presence or absence of an oxidizing agent such as air in an organic solvent including an alcohol such as ethanol and/or an amide such as dimethylformamide, N,N-dimethylacetamide and N,N-dimethylimidazolidin-2-one to give a compound represented by formula (2) or (3). A halogenated central metal in formula (2) may be treated with an alkylating or arylating agent to provide a compound represented by formula (2) or (3) in which a central metal is substituted with alkyl or aryl.

Any of $R^1$ to $R^{12}$ which is hydrogen in formula (2) may undergo a common synthetic process such as nitration, halogenation, formylation, amination, carboxylation, hydroxylation, acylation and elimination for replacement with an appropriate substituent and further, if necessary, another common synthetic process such as reduction, oxidation, isomerization and rearrangement to provide a compound represented by formula (2) or (3).

Examples of porphycenes represented by general formulas (2) and (3) include Compounds (1-1) to (1-64) shown in Table 1 where substituents for Formula (2) are indicated, but substituents for Formula (3) are included in them and corresponding substituents may be of course interchangeable.

TABLE 1

| No. | R¹, R⁷ | R², R⁸ | R³, R⁹ | R⁴, R¹⁰ | R⁵, R¹¹ | R⁶, R¹² | M |
|---|---|---|---|---|---|---|---|
| 1-1 | —CH₃ | H | H | —CH₃ | H | H | H₂ |
| 1-2 | —C₃H₇ | H | H | —C₃H₇ | H | H | 1-methylimidazole-Fe |
| 1-3 | —C₂H₅ | —C₂H₅ | —C₂H₅ | —C₂H₅ | H | H | Cu |
| 1-4 | —C₂H₅ | —C₂H₅ | —C₂H₅ | —C₂H₅ | H | H | Zn |
| 1-5 | —C₂H₅ | —C₂H₅ | —C₂H₅ | —C₂H₅ | H | H | Co |
| 1-6 | —C₂H₅ | —C₂H₅ | —C₂H₅ | —C₂H₅ | H | H | Ni |
| 1-7 | —C₂H₅ | —C₂H₅ | —C₂H₅ | —C₂H₅ | H | H | FeCl |
| 1-8 | —C₂H₅ | —C₂H₅ | —C₂H₅ | —C₂H₅ | H | H | MnCl |
| 1-9 | H | H | H | H | —C₃H₇ | —C₃H₇ | H₂ |
| 1-10 | H | H | H | H | —C₃H₇ | —C₃H₇ | Ni |
| 1-11 | H | H | H | H | H | H | Co |
| 1-12 | H | H | H | H | H | H | Ni |
| 1-13 | —OC₂H₅ | —OC₂H₅ | —OC₂H₅ | —OC₂H₅ | H | H | Co |
| 1-14 | —C₂H₅ | Br | Br | —C₂H₅ | H | H | Zn |
| 1-15 | | | | | H | H | |
| 1-16 | mesityl | mesityl | mesityl | mesityl | H | H | VO |
| 1-17 | —CH₃ | —CH₃ | —CH₃ | —CH₃ | —CH₃ | —CH₃ | TiO |
| 1-18 | benzyl | benzyl | benzyl | benzyl | H | H | Si(OMe)₂ |
| 1-19 | —CH=CH₂ | —CH=CH₂ | —CH=CH₂ | —CH=CH₂ | H | H | Pd |
| 1-20 | —CO₂C₂H₅ | —C₄H₉(t) | Br | —C₂H₅ | H | H | Mg |
| 1-21 | —O—iPr | —O—iPr | —O—iPr | —O—iPr | H | H | Cu |

TABLE 1-continued

| No. | | | | | | | Metal |
|---|---|---|---|---|---|---|---|
| 1-22 | —CH₃ | [2,6-dimethylphenoxy] | —CH₃ | [2,6-dimethylphenoxy] | H | H | Mn |
| 1-23 | —CH₂—CH₂—CH₂—CH₂— | | —CH₂—CH₂—CH₂—CH₂— | | H | H | Cu |
| 1-24 | —CH₂—CH₂—CH₂—CH₂— | | —CH₂—CH₂—CH₂—CH₂— | | H | H | Zn |
| 1-25 | —CH₂—CHCl—CHCl—CH₂— | | —CH₂—CHCl—CHCl—CH₂— | | H | H | FeCl |
| 1-26 | —CH₂—CH₂—CH₂—CH₂— | | —CH₂—CH₂—CH₂—CH₂— | | H | H | MnCl |
| 1-27 | —CH₂—CH₂—CH₂—CH₂— | | —CH₂—CH₂—CH₂—CH₂— | | H | H | Co |
| 1-28 | —CH₂—CH₂—CH₂—CH₂— | | —CH₂—CH₂—CH₂—CH₂— | | H | H | Ni |
| 1-29 | —CCl=CH—CH=CCl— | | —CH=CH—CH=CH— | | H | H | Co |
| 1-30 | —C₂H₅ | —OCH₂OC₂H₅ | —C₂H₅ | —OCH₂OC₂H₅ | H | H | Zn(pyridine)₂ |
| 1-31 | —CH₃ | [1-naphthyloxy] | —CH₃ | [1-naphthyloxy] | H | H | VO |
| 1-32 | —C₄H₉(t) | [2-thienyl] | —C₃H₇ | [2-thienyl] | —C₃H₇ | H | Ni |
| 1-33 | —C₄H₉(t) | [4-methylphenylthio] | H | [4-methylphenyl] | [4-methylphenyl] | H | FeCl |
| 1-34 | H | [cyclohexyl] | H | H | H | H | MnCl |
| 1-35 | Br | [sec-alkyl] | Br | [sec-alkyl] | H | H | Co |
| 1-36 | —C₆H₁₃(t) | —C₆H₁₃(t) | —C₆H₁₃(t) | —C₆H₁₃(t) | H, Br | H, Br | Ni |

TABLE 1-continued

| No. | $R^1, R^7$ | $R^2, R^8$ | $R^3, R^9$ | $R^4, R^{10}$ | $R^5$ | $R^6, R^{11}, R^{12}$ | M |
|---|---|---|---|---|---|---|---|
| 1-37 | —CH₂—O—CH₂CH(C₂H₅)C₄H₉ | —C₂H₅ | —C₂H₅ | —CH₂CH(C₂H₅)C₄H₉ | —C₃H₇ | | Co |
| 1-38 | cyclohexyl | —C₃H₇(i) | —C₃H₇(i) | cyclohexyl | H | | Co |
| 1-39 | —C₄H₉(t) | —CH₂—O—CH₂—O—CH₂—O—CH₃ | —CH₂—O—CH₂—O—CH₂—O—CH₃ | —C₄H₉(t) | H | | Zn |
| 1-40 | —CH₂CH(CH₃)₂ | —CH(iPr)CH(iPr)— | —CH(iPr)CH(iPr)— | —CH₂CH(CH₃)₂ | —C₃H₇ | | Co |
| 1-41 | —C₄H₉(t) | —CH₂CH(C₂H₅)C₄H₉ | —CH₂CH(C₂H₅)C₄H₉ | —C₄H₉(t) | —C₃H₇ | | Cu |
| 1-42 | —C₃H₇ | 4-tBu-C₆H₄— | 4-tBu-C₆H₄— | —C₃H₇ | —C₃H₇ | | Mn |
| 1-43 | —C₃H₇ | H | H | —C₃H₇ | —NO₂ | H | Fe (C₆H₅) |
| 1-44 | —C₃H₇ | H | H | —C₃H₇ | —NH₂ | H | Fe (3,5-F₂-C₆H₃) |
| 1-45 | —C₃H₇ | H | H | —C₃H₇ | —OH | H | Fe(CO) |

TABLE 1-continued

| | | | | | | | |
|---|---|---|---|---|---|---|---|
| 1-46 | —C₂H₅ | —C₂H₅ | —C₂H₅ | —C₂H₅ | | | Co—CH₃ |
| 1-47 | —C₃H₇ | H | H | —C₃H₇ | —SCH₃ | H | Fe—CH₃ |
| 1-48 | —C₂H₄OCH₃ | | | —C₂H₄OCH₃ | —CN | H | [2,4,6-trifluorophenyl]-Fe |
| | | | | | [CH₃C(=O)NH—*] | | |
| 1-49 | —C₂H₄OCH₃ | H | H | —C₂H₄OCH₃ | —N(CH₃)₂ | H | [pentafluorophenyl]-Fe |
| 1-50 | —C₂H₅ | —C₂H₅ | —C₂H₅ | —C₂H₅ | [PhCH₂O—*] | H | Ru(CO)(C₂H₅OH) |
| 1-51 | —C₃H₇ | H | H | —C₃H₇ | H | H | [phenyl]-Co |
| 1-52 | —C₂H₅ | —C₂H₅ | —C₂H₅ | —C₂H₅ | [C₄H₉NHC(=O)—*] | H | Ru(CO) |
| 1-53 | —C₂H₅ | —C₂H₅ | —C₂H₅ | —C₂H₅ | [(C₄H₉)₂NC(=O)—*] | H | Os(CO) |
| 1-54 | —C₂H₅ | —C₂H₅ | —C₂H₅ | —C₂H₅ | [1-methyl-2-oxy-imidazolyl—*] | H | Co—CH₃ |

TABLE 1-continued

| | | | | | | | |
|---|---|---|---|---|---|---|---|
| 1-55 | —CH₃ | —CH₃ | —CH₃ | —CH₃ | ![allyl ester: *—C(=O)—O—CH₂—CH=CH₂] | H | Co |
| 1-56 | —C₂H₅ | —C₂H₅ | —C₂H₅ | —C₂H₅ | —COOH | H | H₂ |
| 1-57 | —CH₃ | —CH₃ | —CH₃ | —CH₃ | ![benzyl ester: *—C(=O)—O—CH₂—C₆H₅] | H | Cu |
| 1-58 | —C₂H₅ | —C₂H₅ | —C₂H₅ | —C₂H₅ | ![*—O—CH₂—CH=CH₂] | H | Ni |
| 1-59 | —C₂H₅ | —C₂H₅ | —C₂H₅ | —C₂H₅ | —SH | H | H₂ |
| 1-60 | —C₃H₇ | H | H | —C₃H₇ | ![acetate: *—O—C(=O)—CH₃] | H | Fe (with N-methylimidazole axial ligands)₂ |
| 1-61 | —C₂H₅ | —C₂H₅ | —C₂H₅ | —C₂H₅ | ![*—S—CH₂—C₆H₅] | H | H₂ |
| 1-62 | —C₂H₅ | —C₂H₅ | —C₂H₅ | —C₂H₅ | ![*—S—CH₂CH₂—CH=CH₂] | H | H₂ |
| 1-63 | —C₂H₅ | —C₂H₅ | —C₂H₅ | —C₂H₅ | ![acetate: *—O—C(=O)—CH₃] | H | H₂ |
| 1-64 | —C₂H₅ | —C₂H₅ | —C₂H₅ | —C₂H₅ | ![phenyl ester: *—C(=O)—O—C₆H₅] | H | H₂ |

The symbol "*" denotes a bonding position.

A dye in a recording layer in an optical recording medium of this invention substantially consists of at least one porphycene particularly selected from those represented by formulas (1) to (3). The compound may be, if necessary, mixed with a compound other than those above described which has an absorption maximum at a wavelength of 290nm to 690nm and exhibits a large refractive index in the range of 300 nm to 700 nm. Examples of such a compound include cyanines, squaliriums, naphthoquinones, anthraquinones, tetrapyraporphyrazines, indophenols, pyryliums, thiopyryliums, azuleniums, triphenylmethanes, xanthenes, indathrenes, indigos, thioindigos, melocyanines, thiazines, acridines, oxazine, dipyrromethenes, oxazoles, azaporphyrin and porphyrins. A mixture of two or more of them may be used and their mixing ratios are about from 0.1 wt % to 30 wt %.

In depositing a recording layer, an additive such as quenchers, thermal decomposition accelerators, ultraviolet absorbers, adhesives, endothermic or endothermically-decomposing compounds and solubility-improving polymers may be, if necessary, added to a compound represented by formula (1). Alternatively, a compound exhibiting such an effect may be introduced into a compound represented by formula (1) as a substituent.

Preferable examples of a quencher include metal complexes such as acetylacetonates, bis(dithiols) including bis-dithio-α-diketones and bis(phenyldithiols), thiocatechols, salicylaldehyde oximes, and thiobisphenolates. Amines may be suitably used.

There are no restrictions to a thermal-decomposition accelerator as long as its accelerating effect on thermal decomposition of a compound can be determined by an appropriate method such as thermal reduction analysis (TG analysis); for example, metal compounds such as metal antiknock agents, metallocenes and acetylacetonate complexes. Examples of a metal antiknock agent include tetraethyl lead or other lead compounds and Mn compounds such as cymantrene [Mn($C_5H_5$)(CO)$_3$]. Examples of a metallocene compound include iron-biscyclopentadienyl complex (ferrocene); and biscyclopentadienyl complexes of Ti, V, Mn, Cr, Co, Ni, Mo, Ru, Rh, Zr, Lu, Ta, W, Os, Ir, Sc and Y. Among others, ferrocene, ruthenocene, osmocene, nickelocene, titanocene and their derivatives exhibit good thermal decomposition effect.

Other examples of a iron-metal compound include organic iron compounds such as iron formate, iron oxalate, iron laurate, iron naphthenate, iron stearate and iron acetate; chelate iron complexes such as acetylacetonate-iron complex, phenanthroline-iron complex, bispyridine-iron complex, ethylenediamine-iron complex, ethylenediamine tetraacetate-iron complex, diethylenetriamine-iron complex, diethyleneglycol dimethyl ether-iron complex, diphosphino-iron complex and dimethylglyoximato-iron complex; iron complexes such as carbonyl-iron complex, cyano-iron complex and ammine-iron complex; halogenated irons such as ferrous chloride, ferric chloride, ferrous bromide and ferric bromide; inorganic iron salts such as iron nitrate and iron sulfate; and iron oxides. A thermal-decomposition accelerator used herein is desirably soluble in an organic solvent and exhibits good moisture resistance, heat resistance and light resistance.

Examples of an endothermic or endothermically decomposing compound include those described in JP-A 10-291366 and those having substituents described in the publication.

The above various quenchers, thermal-decomposition accelerators and endothermic/endothermically-decomposing compounds may be, if necessary, used alone or in combination of two or more.

Alternatively, a compound acting as a quencher, thermal-decomposition accelerator, ultraviolet absorber or adhesive may be introduced into a compound represented by formula (1).

Specifically, a compound residue acting as a quencher, thermal-decomposition accelerator, ultraviolet absorber, adhesive or endothermic/endothermically-decomposing agent may be chemically bound to a porphycene residue represented by formula (1) of this invention via at least one single, double or triple bond to form a single molecule. Preferably, substituents $R^1$ to $R^{12}$ in a porphycene compound represented by formula (2) are independently a substituent represented by formula (11):

$$-(L^n)-(J^n) \tag{11}$$

wherein $L^n$ represents a linker to the porphycene compound represented by formula (2), i.e., a single bond or an optionally substituted methylene, methine, amino, imino or atom chain having 1 to 20 atoms interrupted by at least one of oxygen and sulfur; and $J^n$ represents a compound residue corresponding to any of $R^1$ to $R^{12}$ acting as a quencher, thermal-decomposition accelerator, ultraviolet absorber, adhesive or endothermic/endothermically-decomposing agent. Alternatively, a combination of adjacent substituents in formula (2), i.e., $R^1$ and $R^2$, $R^3$ and $R^4$, $R^5$ and $R^6$, $R^7$ and $R^8$, $R^9$ and $R^{10}$, $R^{11}$ and $R^{12}$, $R^{12}$ and $R^1$, $R^2$ and $R^3$, $R^4$ and $R^5$, $R^6$ and $R^7$, $R^8$ and $R^9$ or $R^{10}$ and $R^{11}$ may be a moiety represented by formula (12)

$$-(L^{m1})-(J^m)-(L^{m2})- \tag{12}$$

wherein $L^{m1}$ and $L^{m2}$ are mutually adjacent and represent a linker to the porphycene compound represented by formula (2), i.e., a single bond or an optionally substituted methylene, methine, amino, imino or atom chain having 1 to 20 atoms interrupted by at least one of oxygen and sulfur; and $J^m$ represents a compound residue corresponding to any of $R^1$ to $R^{12}$ acting as a quencher, thermal-decomposition accelerator, ultraviolet absorber, adhesive or endothermic/endothermically-decomposing agent.

Preferable examples of an atom chain for $L^n$, $L^{m1}$ and $L^{m2}$ include a single bond, —C(=O)—OCH$_2$—, —C(=O)—OCH(CH$_3$)—, —OCH$_2$—, —OCH(CH$_3$)—, —CH$_2$OCH$_2$—, —CH$_2$OCH(CH$_3$)—, —CH(CH$_3$)OCH(CH$_3$)—, —O—C(=O)—, —CH=CH—, —CH=N—, —C(=O)—, —CH=CH—C(=O)O— and —C(C=O)CH$_2$CH$_2$C(=O)—O—.

Preferable examples of $J^n$ and $J^m$ include metallocene residues such as ferrocene residue, cobaltocene residue, nickelocene residue, ruthenocene residue, osmocene residue and titanocene residue.

Suitable examples of a structure for formula (11) include the following metal complex residues:

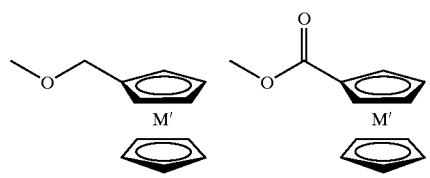

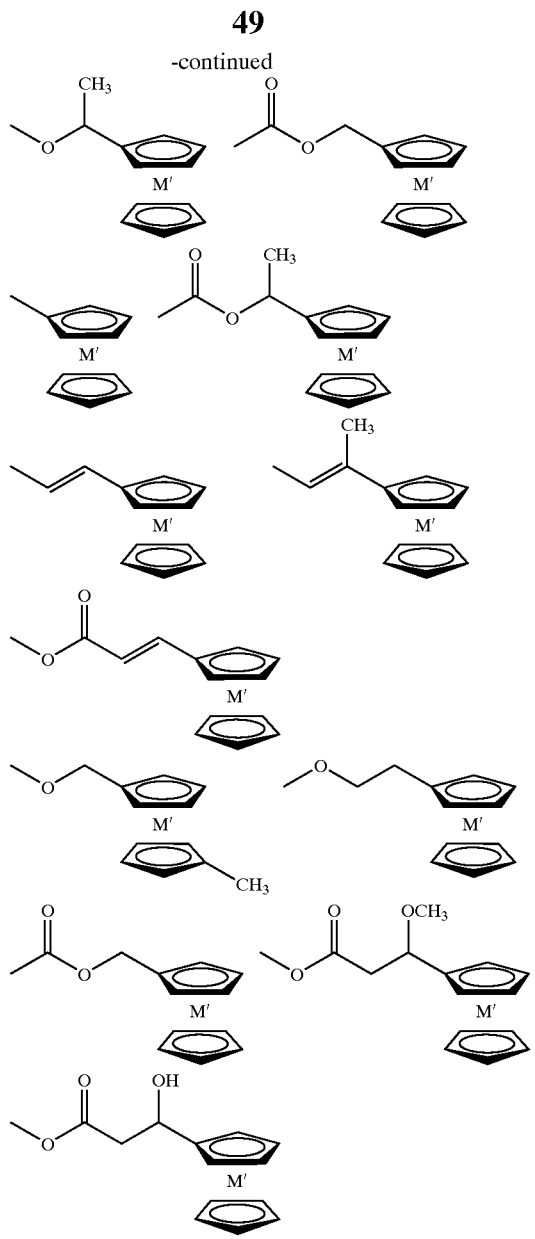

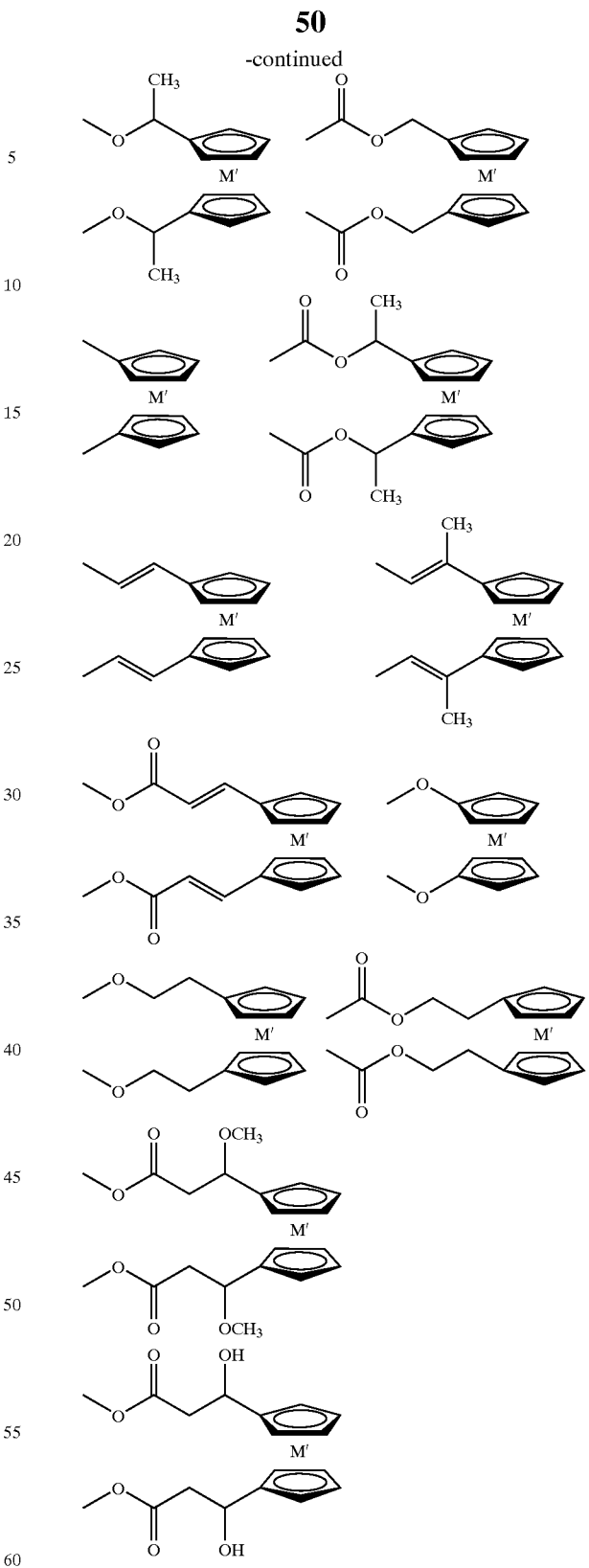

wherein M' represents Fe, Ru, Co, Ni, Os or M"Z'$_2$; M" represents Ti, Zr, Hf, Nb, Mo or V; Z' represents CO, F, Cl, Br, I, or alkyl, alkoxy, aryl, aryloxy, aralkyl or aralkyloxy having 1 to 10 carbon atoms and optionally having a substituent as defined for $R^1$ to $R^{12}$.

Suitable examples of a structure for formula (12) include the following metal complex residues:

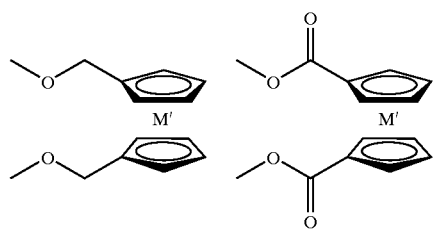

wherein M' represents Fe, Ru, Co, Ni, Os or M"Z'$_2$; M" represents Ti, Zr, Hf, Nb, Mo or V; Z' represents CO, F, Cl, Br, I, or alkyl, alkoxy, aryl, aryloxy, aralkyl or aralkyloxy having 1 to 10 carbon atoms and optionally having a substituent as defined for $R^1$ to $R^{12}$.

If necessary, an additive such as binders, leveling agents and antifoams may be added. Preferable examples of a binder include polyvinyl alcohol, polyvinylpyrrolidone, nitrocellulose, cellulose acetate, ketone resins, acrylate resins, polystyrene resins, urethane resins, polyvinylbutyral, polycarbonates and polyolefines.

During deposition of a recording layer on a substrate, a layer made of an organic material or polymer may be formed on the substrate in order to improve solvent resistance, a reflectance and/or a recording sensitivity of the substrate.

The content of a compound represented by general formula (1) in the recording layer may be appropriately selected from the range where recording and reproduction can be conducted; generally at least 30 wt %, preferably at least 60 wt %. It is also preferable that the content is substantially 100 wt %.

The recording layer may be formed by an appropriate method including application processes such as spin coating, spraying, casting, sliding, curtain, extrusion, wire, gravure, spread, roller-coating, knife and immersion techniques; sputtering; chemical vapor deposition; and vacuum deposition. Spin coating is preferable because of its convenience.

Using an application process such as spin coating, a compound represented by general formula (1) is dissolved or dispersed in a solvent to 1 to 40 wt %, preferably 3 to 30 wt % to prepare an application liquid. It is preferable to chose a solvent which does not harmful to a substrate. Examples of a solvent which may be used include alcohols such as methanol, ethanol, isopropyl alcohol, octafluoropentanol, allyl alcohol, methylcellosolve, ethylcellosolve and tetrafluoropropanol; aliphatic or alicyclic hydrocarbons such as hexane, heptane, octane, decane, cyclohexane, methylcyclohexane, ethylcyclohexane and dimethylcyclohexane; aromatic hydrocarbons such as toluene, xylene and benzene; halogenated hydrocarbons such as carbon tetrachloride, chloroform, tetrachloroethane and dibromoethane; ethers such as diethyl ether, dibutyl ether, diisopropyl ether and dioxane; ketones such as acetone and 3-hydroxy-3-methyl-2-butanone; esters such as ethyl acetate and methyl lactate; and water, which may be used alone or in combination of two or more.

A compound for a recording layer may be, if necessary, dispersed in a polymer film for use.

When a solvent not harmful to a substrate cannot be chosen, sputtering, chemical vapor deposition or vacuum deposition is effective.

A film thickness of the recording layer is 30 nm to 1000 nm, preferably 50 nm to 300 nm. If the recording layer is thinner than 30 nm, thermal diffusion may be too large to conduct recording or a recording signal may be distorted and a signal amplitude may be reduced. If the film is thicker than 1000 nm, a reflectance may be lowered, leading to deterioration in reproduction signal properties.

Then, on the recording layer is formed a reflecting layer with a thickness of preferably 50 nm to 300 nm. A reflection amplifying layer or adhesion layer may be formed between the recording and the reflecting layers for improving a reflectance or adhesiveness. A material for the reflecting layer may be selected from those exhibiting an adequately high reflectance at a wavelength of a reproduction light. For example, metals such as Au, Al, Ag, Cu, Ti, Cr, Ni, Pt, Ta and Pd may be used alone or as an alloy. Among them, Au, Ag and Al are suitable as a material for the reflecting layer because of their higher reflectance. When conducting recording/reproduction with a blue laser, Al or Ag is suitable. Besides those described above, other materials may be incorporated; for example, metals and metalloids such as Mg, Se, Hf, V, Nb, Ru, W, Mn, Re, Fe, Co, Rh, Ir, Zn, Cd, Ga, In, Si, Ge, Te, Pb, Po, Sn and Bi. A material containing Ag or Al as a main component is suitable because it may allow a reflecting layer with a higher reflectance to be easily provided. Films with a lower refractive index and a higher refractive index made of materials other than a metal may be alternately laminated to form a multilayer film, which may be used as a reflecting layer.

The reflecting layer may be formed by an appropriate process such as sputtering, ion plating, chemical vapor deposition and vacuum deposition. An intermediate layer and/or an adhesive layer made of well-known inorganic or organic materials may be formed on the substrate and/or under the reflecting layer for improving a reflectance, recording properties and adhesiveness.

There are no restrictions to a protective layer formed on the reflecting layer as long as it can protect the reflecting layer from external force. Examples of a material for the protective layer include inorganic materials such as $SiO_2$, $Si_3N_4$, $MgF_2$, AlN and $SnO_2$; and organic materials such as thermoplastic resins, thermosetting resins, electron-beam curing resins and ultraviolet curing resins. A thermoplastic or thermosetting resin may be dissolved in an appropriate solvent to prepare an application liquid. The liquid may be applied and dried to form a film. An ultraviolet curing resin may be used as it is or dissolved in an appropriate solvent to prepare an application liquid. Then the liquid is applied and cured by irradiation of ultraviolet rays to form a film. Examples of an ultraviolet curing agent include acrylate resins such as urethane acrylates, epoxy acrylates and polyester acrylates. These materials may be used alone or in combination and may form a single layer or a multilayer film.

The protective layer may be formed by an application process such as spin coating and casting; sputtering; or chemical vapor deposition as is for the recording layer. In particular, spin coating is preferable.

A film thickness of the protective layer is generally 0.1 $\mu$m to 100 $\mu$m, but in this invention it is 3 $\mu$m to 30 $\mu$m, more preferably 5 $\mu$m to 20 $\mu$m.

A label or bar code may be further printed on the protective layer.

A protective sheet or substrate may be laminated on the reflective layer. Alternatively, two optical recording media may be laminated such that the inside planes of two reflective layers may mutually face.

On the mirror face of the substrate, an ultraviolet curing resin or inorganic film may be deposited for surface protection and prevention of impurities such as dusts from adhering to the surface.

Figure 3:
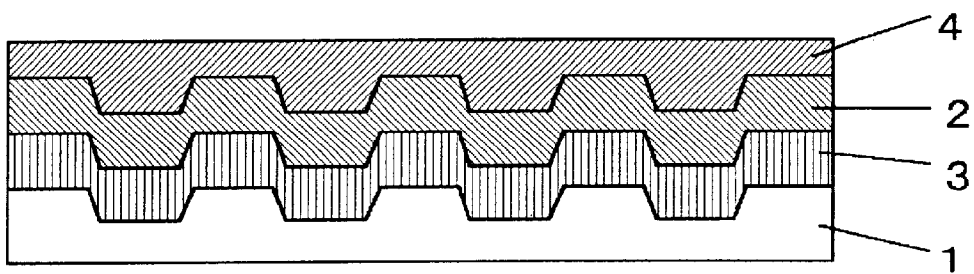
FIG. 3 schematically shows a still other example for a configuration of an optical recording medium according to this invention.

When preparing an optical recording medium illustrated in FIG. 3, a reflecting layer is formed on a substrate to a thickness of preferably 1 nm to 300 nm. A reflection amplifying layer or adhesion layer may be formed between the recording and the reflecting layers for improving a reflectance or adhesiveness. A material for the reflecting layer may be selected from those exhibiting an adequately high reflectance at a wavelength of a reproduction light. For example, metals such as Al, Ag, Ni and Pt may be used alone or as an alloy. Among them, Ag and Al are suitable as a material for the reflecting layer because of their higher reflectance. When conducting recording/reproduction with a blue laser, Al or Ag is suitable. Besides those described above, other materials may be, if necessary, incorporated; for example, metals and metalloids such as Mg, Se, Hf, V, Nb, Ru, W, Mn, Re, Fe, Co, Rh, Ir, Zn, Cd, Ga, In, Si, Ge, Te, Pb, Po, Sn, Bi, Au, Cu, Ti, Cr, Pd and Ta. A material containing Ag or Al as a main component is suitable because it may allow a reflecting layer with a higher reflectance to be easily provided. Films with a lower refractive index and a higher refractive index made of materials other than a metal may be alternately laminated to form a multilayer film, which may be used as a reflecting layer.

The reflecting layer may be formed by an appropriate process such as sputtering, ion plating, chemical vapor deposition and vacuum deposition. An intermediate layer and/or an adhesive layer made of well-known inorganic or organic materials may be formed on the substrate and/or under the reflecting layer for improving a reflectance, recording properties and adhesiveness.

Then, during deposition of a recording layer on a reflecting layer, a layer made of an organic material or polymer may be formed on the reflecting layer in order to improve solvent resistance, a reflectance and/or a recording sensitivity of the reflecting layer.

The content of a compound represented by general formula (1) in the recording layer may be appropriately selected from the range where recording and reproduction can be conducted; generally at least 30 wt %, preferably at least 60 wt %. It is also preferable that the content is substantially 100 wt %.

The recording layer may be formed by an appropriate method including application processes such as spin coating, spraying, casting, sliding, curtain, extrusion, wire, gravure, spread, roller-coating, knife and immersion techniques; sputtering; chemical vapor deposition; and vacuum deposition. Spin coating is preferable because of its convenience.

Using an application process such as spin coating, a compound represented by general formula (1) is dissolved or dispersed in a solvent to 1 to 40 wt %, preferably 3 to 30 wt % to prepare an application liquid. It is preferable to chose a solvent which does not harmful to a reflecting layer. Examples of a solvent which may be used include alcohols such as methanol, ethanol, isopropyl alcohol, octafluoropentanol, allyl alcohol, methylcellosolve, ethylcellosolve and tetrafluoropropanol; aliphatic or alicyclic hydrocarbons such as hexane, heptane, octane, decane, cyclohexane, methylcyclohexane, ethylcyclohexane and dimethylcyclohexane; aromatic hydrocarbons such as toluene, xylene and benzene; halogenated hydrocarbons such as carbon tetrachloride, chloroform, tetrachloroethane and dibromoethane; ethers such as diethyl ether, dibutyl ether, diisopropyl ether and dioxane; ketones such as acetone and 3-hydroxy-3-methyl-2-butanone; esters such as ethyl acetate and methyl lactate; and water, which may be used alone or in combination of two or more.

A compound for a recording layer may be, if necessary, dispersed in a polymer film for use.

When a solvent not harmful to a reflecting layer cannot be chosen, sputtering, chemical vapor deposition or vacuum deposition is effective.

A film thickness of the recording layer in the case of this medium structure is generally 1 nm to 1000nm, preferably 5 nm to 300 nm. If the recording layer is thinner than 1 nm, recording may not be conducted or a recording signal may be distorted and a signal amplitude may be reduced. If the film is thicker than 1000 nm, a reflectance may be lowered, leading to deterioration in reproduction signal properties.

There are no restrictions to a protective layer formed on the reflecting layer as long as it can protect the recording layer from external harmful effects such as external force and the ambient atmosphere. Examples of a material for the protective layer include inorganic materials such as $SiO_2$, $Si_3N_4$, $MgF_2$, AlN and $SnO_2$; and organic materials such as thermoplastic resins, thermosetting resins, electron-beam curing resins and ultraviolet curing resins. A thermoplastic or thermosetting resin may be dissolved in an appropriate solvent to prepare an application liquid. The liquid may be applied and dried to form a film. An ultraviolet curing resin may be used as it is or dissolved in an appropriate solvent to prepare an application liquid. Then the liquid is applied and cured by irradiation of ultraviolet rays to form a film. Examples of an ultraviolet curing agent include acrylate resins such as urethane acrylates, epoxy acrylates and polyester acrylates. These materials may be used alone or in combination and may form a single layer or a multilayer film.

The protective layer may be formed by an application process such as spin coating and casting; sputtering; or chemical vapor deposition as is for the recording layer. In particular, spin coating is preferable.

A film thickness of the protective layer may be generally 0.01 $\mu$m to 1000 $\mu$m, sometimes 0.1 $\mu$m to 100 $\mu$m, particularly 1 $\mu$m to 20 $\mu$m.

A protective sheet or reflecting layer may be laminated on the substrate. Alternatively, two optical recording media may be laminated such that the inside planes of two substrates may mutually face.

On the protective-layer side, an ultraviolet curing resin or inorganic film may be deposited for surface protection and prevention of impurities such as dusts from adhering to the surface.

For an optical recording medium of this invention, a case type of protection unit protecting a disk as used in a floppy disk or magneto-optical disk may be used for protecting the whole medium. The unit may be made of a plastic or a metal such as aluminum.

A substrate may be made of a material basically transparent at wavelengths of a recording and a reproduction beams. A supporting substrate may be made of a transparent material including polymers such as acrylate resins, polyethylene resins, polycarbonate resins, polyolefin resins and epoxy resins and inorganic materials such as glass, considering the case as shown in FIG. 4 where a blue-violet laser irradiation is conducted through a substrate 11. On the other hand, when laser irradiation is conducted from the side of a light transmitting layer 15' opposite to a substrate 11' as shown in FIG. 5, a material for the substrate must not meet optical requirements and may be selected from a wide range of materials. In the light of mechanical properties required in a substrate and productivity of the substrate, a material which may be formed by injection molding or casting is preferable; for example, acrylate resins, polycarbonate resins and polyolefin resins. These materials may be formed into a disk substrate by, for example, injection molding.

On an upper layer of such a substrate, guide grooves and/or prepits with a submicron order may be formed helically or concentrically. These guide grooves and prepits are preferably formed during preparing a substrate, and may be formed by, for example, injection molding using a stumper template or heat transfer printing using a photopolymer. Furthermore, guide grooves and/or prepits may be formed in a light transmitting layer 15' in FIG. 5, by a method as described above. A pitch and a depth of the guide groove is preferably selected from the ranges of 0.25 to 0.80 $\mu$m for a pitch and of 20 to 150 nm for a depth, for an HD-DVDR in which recording is conducted with a higher density than a DVD.

When used as an optical disk, a substrate may be a disk with a thickness of about 1.2 mm and a diameter of about 80 to 120 mm, and may have an opening with a diameter of about 15 mm in its center.

A laser with wavelengths of 300 nm to 500 nm and 500 nm to 700 nm in this invention may be a dye laser whose wavelength may be selected from a wide visible-light range; a gas laser such as He—Ne laser (633 nm) and nitrogen laser (337 nm); an ion laser such as helium-cadmium laser at 445 nm and argon laser at 457 or 488 nm; GaN laser at 400 to 410 nm; a laser emitting a second harmonic 430 nm of an infrared laser at 860 nm using Cr-doped $LiSnAlF_6$; or a semiconductor laser such as a visible semiconductor laser at 415, 425, 602, 612, 635, 647, 650, 660, 670 or 680 nm. In this invention, the above devices such as a semiconductor laser may be appropriately selected, depending on a wavelength to which a recording layer conducting recording or reproduction responds. High-density recording and reproduction may be individually conducted at a single wavelength or a plurality of wavelengths selected from the above semiconductor lasers.

EXAMPLES

This invention will be described with reference to examples, but this invention is not limited to these in any manner.

Example 1

Compound (1-1) listed in Table 1, a compound represented by general formula (1) was deposited on a polycarbonate disk substrate with an outer diameter of 120 mmϕ and a thickness of 0.6 mm having a continuous guide groove (track pitch: 0.74 μm) to 70 nm by vacuum deposition.

On the recording layer was sputtered silver using a sputtering apparatus (CDI-900; Balzas) to form a reflecting layer with a thickness of 100 nm. A sputtering gas was argon. Sputtering was conducted under the conditions of sputtering power: 2.5 kW and sputtering gas pressure: 1.33 Pa ($1.0 \times 10^{-2}$ Torr).

After spin-coating an ultraviolet curing resin SD-17 (Dainippon Ink And Chemicals, Incorporated) on the reflecting layer, the product was irradiated with ultraviolet rays to form a protective film with a thickness of 5 μm. Then, after spin-coating an ultraviolet curing resin SD-301 (Dainippon Ink And Chemicals, Incorporated) on the protective layer, the same polycarbonate resin substrate as described above except lack of a guide groove was laminated. These substrates were adhered by ultraviolet irradiation to give an optical recording medium.

The optical recording medium comprising a recording layer thus formed was evaluated as follows.

An evaluation device equipped with a blue laser head with a wavelength of 403 nm and an N.A. of 0.65 was used to conducted recording under the conditions of recording frequency: 9.7 MHz, recording laser power: 8.5 mW, linear velocity: 9.0 m/s and minimum pit length: 0.46 μm. Pit formation and recording were satisfactory. After recording, the same evaluation device was used to conduct reproduction under the conditions of reproduction laser power: 0.6 mW and linear velocity: 9.0 m/s. The pit could be read out. After repeating reproduction 1000 or more times, the pit could be read out, indicating good reproduction light stability.

A light resistance test was conducted, in which the test sample was irradiated with Xe light of 40,000 lux for 100 hours. After the test, the pit could be read out.

A humidity/heat resistance test was conducted for 200 hours, in which the sample was left under the atmosphere of humidity: 85%RH and temperature: 80° C. After the test, the pit could be read out.

Example 2

On the optical recording medium prepared in Example 1, recording and reproduction were conducted as described in Example 1 except that a recording laser power was 6.5 mW. A pit was satisfactorily formed and read out as was in Example 1. Furthermore, it exhibited good reproduction light stability.

After a light resistance and a humidity/heat resistance test, the pit could be read out.

Example 3

On the optical recording medium prepared in Example 1, recording and reproduction were conducted as described in Example 1 except that a recording laser power was 6.5 mW. A pit was satisfactorily formed and read out. Furthermore, it exhibited good reproduction light stability.

After a light resistance and a humidity/heat resistance test, the pit could be read out.

Example 4

For evaluation of the optical recording medium prepared as described in Example 1, an evaluation device equipped with a semiconductor laser head at 660 nm for a thickness of 0.6 mm was used to conduct recording and reproduction under the conditions of linear velocity: 3.5 m/s, recording laser power: 8 mW and minimum pit length: 0.40 μm. A pit was satisfactorily formed and recorded. After recording, the same evaluation device was used to conduct reproduction and the pit could be read out. Furthermore, reproduction light stability was good.

After a light resistance and a humidity/heat resistance test, the pit could be read out.

Examples 5 to 37

Optical recording media were prepared and used for recording and reproduction as described in Example 1, except that Compounds (1-2) to (1-34) listed in Table 1 were used as a recording layer. A pit was satisfactorily formed and read out. Furthermore, reproduction light stability was good.

After a light resistance and a humidity/heat resistance test, the pit could be read out.

Examples 38 to 70

Optical recording media were prepared as described in Example 1 and used for recording and reproduction as described in Example 4, except that Compounds (1-2) to (1-34) listed in Table 1were used as a recording layer. A pit was satisfactorily formed and read out. Furthermore, reproduction light stability was good.

After a light resistance and a humidity/heat resistance test, the pit could be read out.

Example 71

In 10 mL of dimethylcyclohexane was dissolved Compound (1–35) listed in Table 1 for a recording layer to prepare a dye solution. A substrate used was a polycarbonate disk with an outer diameter of 120 mmϕ and a thickness of 0.6 mm having a continuous guide groove (track pitch: 0.74 μm). On the substrate was spin-coated the dye solution at a rotation rate of 1500 $min^{-1}$ and the substrate was dried at 70° C. for 3 hours to form a recording layer. On the recording layer was sputtered silver using a sputtering apparatus (CDI-900; Balzas) to form a reflecting layer with a thickness of 100 nm. A sputtering gas was argon. Sputtering was conducted under the conditions of sputtering power: 2.5 kW and sputtering gas pressure: 1.33 Pa ($1.0 \times 10^{-2}$ Torr).

After spin-coating an ultraviolet curing resin SD-17 (Dainippon Ink And Chemicals, Incorporated) on the reflecting layer, the product was irradiated with ultraviolet rays to form a protective film with a thickness of 5 $\mu$m. Then, after spin-coating an ultraviolet curing resin SD-301 (Dainippon Ink And Chemicals, Incorporated) on the protective layer, the same polycarbonate resin substrate as described above was laminated. These substrates were adhered by ultraviolet irradiation to give an optical recording medium.

Recording and reproduction was conducted as described in Example 1. A pit could be satisfactorily formed and read out. Furthermore, reproduction light stability was good.

After a light resistance and a humidity/heat resistance test, the pit could be read out.

Examples 72 to 77

Optical recording media were prepared as described in Example 71 and used for recording and reproduction as described in Example 1, except that Compounds (1-36) to (1-41) listed in Table 1 were used as a recording layer. A pit was satisfactorily formed and readout. Furthermore, reproduction light stability was good.

After a light resistance and a humidity/heat resistance test, the pit could be read out.

Examples 78 to 83

Optical recording media were prepared as described in Example 71 and used for recording and reproduction as described in Example 4, except that Compounds (1-36) to (1-41) listed in Table 1 were used as a recording layer. A pit was satisfactorily formed and read out. Furthermore, reproduction light stability was good.

After a light resistance and a humidity/heat resistance test, the pit could be read out.

Example 84

In 10 mL of 2,2,3,3-tetrafluoropropanol was dissolved Compound(1–42) listed in Table 1 for a recording layer to prepare a dye solution. A substrate used was a polycarbonate disk with an outer diameter of 120 mm$\phi$ and a thickness of 0.6 mm having a continuous guide groove (track pitch: 0.74 $\mu$m). On the substrate was spin-coated the dye solution at a rotation rate of 1500 min-1 and the substrate was dried at 70° C. for 3 hours to form a recording layer. On the recording layer was sputtered silver using a sputtering apparatus (CDI-900; Balzas) to form a reflecting layer with a thickness of 100 nm. A sputtering gas was argon. Sputtering was conducted under the conditions of sputtering power: 2.5 kW and sputtering gas pressure: 1.33 Pa ($1.0 \times 10^{-2}$ Torr).

After spin-coating an ultraviolet curing resin SD-17 (Dainippon Ink And Chemicals, Incorporated) on the reflecting layer, the product was irradiated with ultraviolet rays to form a protective film with a thickness of 5 $\mu$m. Then, after spin-coating an ultraviolet curing resin SD-301 (Dainippon Ink And Chemicals, Incorporated) on the protective layer, the same polycarbonate resin substrate as described above was laminated. These substrates were adhered by ultraviolet irradiation to give an optical recording medium.

Recording and reproduction was conducted as described in Example 1. A pit could be satisfactorily formed and read out. Furthermore, reproduction light stability was good.

After a light resistance and a humidity/heat resistance test, the pit could be read out.

Example 85

An optical recording medium was prepared as described in Example 84 and used for recording and reproduction as described in Example 4. A pit was satisfactorily formed and readout. Furthermore, reproduction light stability was good.

After a light resistance and a humidity/heat resistance test, the pit could be read out.

Examples 86 to 97

Optical recording media were prepared as described in Example 1 and used for recording and reproduction as described in Example 1, except that Compounds (1-43) to (1-54) listed in Table 1 were used as a recording layer. A pit was formed in an outstanding form and it was able to be read by high C/N ratio. Furthermore, reproduction light stability was very good.

After a light resistance and a humidity/heat resistance test, the pit could be read out.

Examples 98 to 107

Optical recording media were prepared as described in Example 1 and used for recording and reproduction as described in Example 1, except that Compounds (1-55) to (1-64) listed in Table 1 were used as a recording layer. A pit was satisfactorily formed and readout. Furthermore, reproduction light stability was good.

After a light resistance and a humidity/heat resistance test, the pit could be read out.

Comparative Example 1

An optical recording medium was prepared as described in Example 84 and used for recording and reproduction as described in Example 1, substituting a compound represented by formula (a):

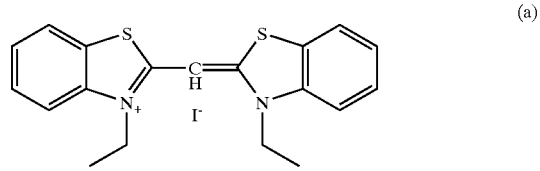

(a)

for Compound (1-42). A C/N ratio was as low as 20 dB or less so that recording could not be conducted.

As described in Examples 1 to 107, an optical recording medium according to this invention can conduct recording and reproduction in both blue laser and red laser wavelength ranges and exhibits good light resistance and humidity/heat resistance.

Thus, a recording layer comprising a compound having a structure defined in this invention can allow us to record a signal using a laser beam at a wavelength selected from the ranges of 300 to 5 nm and/or 500 to 700 nm. An optical recording medium of this invention can be used as an optical recording medium using a laser beam at a wavelength selected from the ranges of 300 to 500 nm and/or 500 to 700 nm for recording and reproduction.

What is claimed is:

1. An optical recording medium having a recording layer comprising at least one compound selected from optionally metal-complexed porphycenes.

2. The optical recording medium as claimed in claim 1 having an organic dye layer as a recording layer on a substrate, comprising at least one compound selected from the compounds as defined in the above (1) in the organic dye layer.

3. The optical recording medium as claimed in claim 2 wherein the porphycene compound is represented by general formula (1):

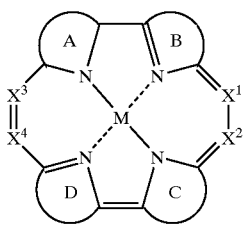

(1)

wherein the rings A, B, C and D independently represent an optionally substituted pyrrole ring; $X^1$, $X^2$, $X^3$ and $X^4$ independently represents optionally substituted methine group; and M represents two hydrogen atoms, a bivalent to tetravalent metal, metalloid or oxymetal atom optionally having a substituent or ligand.

4. The optical recording medium as claimed in claim 3 wherein the porphycene compound is represented by general formula (2):

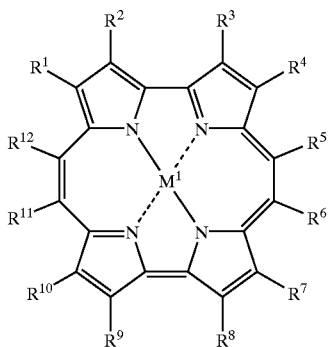

(2)

wherein $R^1$ to $R^{12}$ independently represent hydrogen, halogen, nitro, cyano, hydroxyl, amino, carboxyl, mercapto, substituted or unsubstituted alkyl, aralkyl, aryl, alkenyl, alkoxy, aralkyloxy, aryloxy, alkenyloxy, alkylthio, aralkylthio, arylthio, alkenylthio, acyl, acyloxy, mono-substituted amino, di-substituted amino, alkoxycarbonyl, aralkyloxycarbonyl, aryloxycarbonyl, alkenyloxycarbonyl, mono-substituted aminocarbonyl, di-substituted aminocarbonyl, heteroaryl or heteroaryloxy; or each substituent of $R^1$ to $R^{12}$ together with an adjacent substituent may form a ring through a linking group; and $M^1$ represents two hydrogen atoms, a bivalent to tetravalent metal, metalloid or oxymetal atom optionally having a substituent or ligand.

5. The optical recording medium as claimed in claim 4 wherein the porphycene compound is represented by general formula (3):

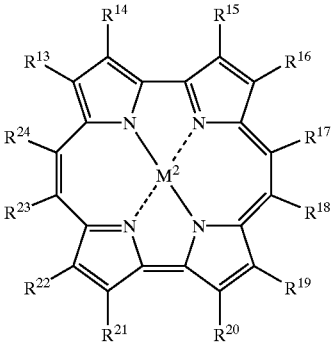

(3)

wherein $R^{13}$ to $R^{24}$ independently represent hydrogen, halogen, nitro, cyano, hydroxyl, amino, carboxyl, mercapto, substituted or unsubstituted alkyl, aralkyl, aryl, alkenyl, alkoxy, aralkyloxy, aryloxy, alkenyloxy, alkylthio, aralkylthio, arylthio, alkenylthio, acyl, acyloxy, mono-substituted amino, di-substituted amino, alkoxycarbonyl, aralkyloxycarbonyl, aryloxycarbonyl, alkenyloxycarbonyl, mono-substituted aminocarbonyl, di-substituted aminocarbonyl, heteroaryl or heteroaryloxy; each of $R^{13}$ to $R^{24}$ together with an adjacent substituent may form a ring through a linking group; $M^2$ is a bivalent to tetravalent metal atom having a substituent selected from the group consisting of alkyl, aryl and heteroaryloxy group and/or a ligand selected from the group consisting of a carbon monoxide and an alcohol.

6. The optical recording medium as claimed in claim 5 capable of recording and reproduction to a laser beam with a wavelength selected from the range of 300 nm to 500 nm and/or 500 nm to 700 nm.

7. The optical recording medium as claimed in claim 6 capable of recording and reproduction to a laser beam with a wavelength selected from the range of 400 nm to 500 nm and/or 600 nm to 700 nm.

8. The optical recording medium as claimed in claim 7 capable of recording and reproduction to a laser beam with a wavelength selected from the range of 400 nm to 410 nm and/or 635 nm to 660 nm.

9. The optical recording medium as claimed in claim 1 wherein the porphycene compound is represented by general formula (1):

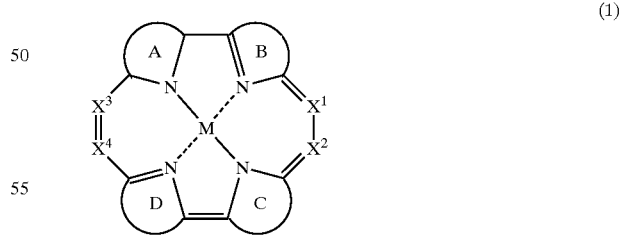

(1)

wherein the rings A, B, C and D independently represent an optionally substituted pyrrole ring; $X^1$, $X^2$, $X^3$ and $X^4$ independently represents optionally substituted methine group; and M represents two hydrogen atoms, a bivalent to tetravalent metal, metalloid or oxymetal atom optionally having a substituent or ligand.

10. The optical recording medium as claimed in claim 9 wherein the porphycene compound is represented by general formula (2):

(2)

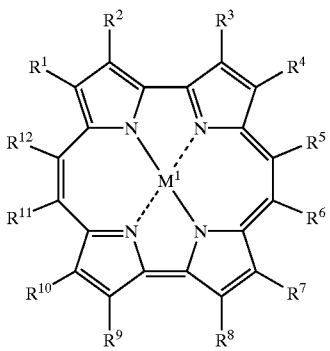

wherein $R^1$ to $R^{12}$ independently represent hydrogen, halogen, nitro, cyano, hydroxyl, amino, carboxyl, mercapto, substituted or unsubstituted alkyl, aralkyl, aryl, alkenyl, alkoxy, aralkyloxy, aryloxy, alkenyloxy, alkylthio, aralkylthio, arylthio, alkenylthio, acyl, acyloxy, mono-substituted amino, di-substituted amino, alkoxycarbonyl, aralkyloxycarbonyl, aryloxycarbonyl, alkenyloxycarbonyl, mono-substituted aminocarbonyl, di-substituted aminocarbonyl, heteroaryl or heteroaryloxy; or each substituent of $R^1$ to $R^{12}$ together with an adjacent substituent may form a ring through a linking group; and $M^1$ represents two hydrogen atoms, a bivalent to tetravalent metal, metalloid or oxymetal atom optionally having a substituent or ligand.

11. The optical recording medium as claimed in claim 10 wherein the porphycene compound is represented by general formula (3):

(3)

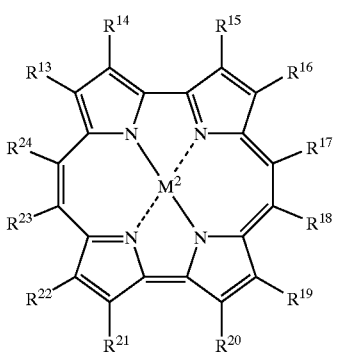

wherein $R^{13}$ to $R^{24}$ independently represent hydrogen, halogen, nitro, cyano, hydroxyl, amino, carboxyl, mercapto, substituted or unsubstituted alkyl, aralkyl, aryl, alkenyl, alkoxy, aralkyloxy, aryloxy, alkenyloxy, alkylthio, aralkylthio, arylthio, alkenylthio, acyl, acyloxy, mono-substituted amino, di-substituted amino, alkoxycarbonyl, aralkyloxycarbonyl, aryloxycarbonyl, alkenyloxycarbonyl, mono-substituted aminocarbonyl, di-substituted aminocarbonyl, heteroaryl or heteroaryloxy; each of $R^{13}$ to $R^{24}$ together with an adjacent substituent may form a ring through a linking group; $M^2$ is a bivalent to tetravalent metal atom having a substituent selected from the group consisting of alkyl, aryl and heteroaryloxy group and/or a ligand selected from the group consisting of a carbon monoxide and an alcohol.

12. The optical recording medium as claimed in claim 6 capable of recording and reproduction to a laser beam with a wavelength selected from the range of 300 nm to 500 nm and/or 500 nm to 700 nm.

13. The optical recording medium as claimed in claim 12 capable of recording and reproduction to a laser beam with a wavelength selected from the range of 400 nm to 500 nm and/or 600 nm to 700 nm.

14. The optical recording medium as claimed in claim 13 capable of recording and reproduction to a laser beam with a wavelength selected from the range of 400 nm to 410 nm and/or 635 nm to 660 nm.

15. The optical recording medium as claimed in claim 1 capable of recording and reproduction to a laser beam with a wavelength selected from the range of 300 nm to 500 nm and/or 500 nm to 700 nm.

16. The optical recording medium as claimed in claim 15 capable of recording and reproduction to a laser beam with a wavelength selected from the range of 400 nm to 500 nm and/or 600 nm to 700 nm.

17. The optical recording medium as claimed in claim 16 capable of recording and reproduction to a laser beam with a wavelength selected from the range of 400 nm to 410 nm and/or 635 nm to 660 nm.

18. The optical recording medium as claimed in claim 2 capable of recording and reproduction to a laser beam with a wavelength selected from the range of 300 nm to 500 nm and/or 500 nm to 700 nm.

19. The optical recording medium as claimed in claim 18 capable of recording and reproduction to a laser beam with a wavelength selected from the range of 400 nm to 500 nm and/or 600 nm to 700 nm.

20. The optical recording medium as claimed in claim 19 capable of recording and reproduction to a laser beam with a wavelength selected from the range of 400 nm to 410 nm and/or 635 nm to 660 nm.

21. The optical recording medium as claimed in claim 3 capable of recording and reproduction to a laser beam with a wavelength selected from the range of 300 nm to 500 nm and/or 500 nm to 700 nm.

22. The optical recording medium as claimed in claim 21 capable of recording and reproduction to a laser beam with a wavelength selected from the range of 400 nm to 500 nm and/or 600 nm to 700 nm.

23. The optical recording medium as claimed in claim 22 capable of recording and reproduction to a laser beam-with a wavelength selected from the range of 400 nm to 410 nm and/or 635 nm to 660 nm.

24. The optical recording medium as claimed in claim 4 capable of recording and reproduction to a laser beam with a wavelength selected from the range of 300 nm to 500 nm and/or 500 nm to 700 nm.

25. The optical recording medium as claimed in claim 24 capable of recording and reproduction to a laser beam with a wavelength selected from the range of 400 nm to 500 nm and/or 600 nm to 700 nm.

26. The optical recording medium as claimed in claim 25 capable of recording and reproduction to a laser beam with a wavelength selected from the range of 400 nm to 410 nm and/or 635 nm to 660 nm.

27. The optical recording medium as claimed in claim 9 capable of recording and reproduction to a laser beam with a wavelength selected from the range of 300 nm to 500 nm and/or 500 nm to 700 nm.

28. The optical recording medium as claimed in claim 27 capable of recording and reproduction to a laser beam with a wavelength selected from the range of 400 nm to 500 nm and/or 600 nm to 700 nm.

29. The optical recording medium as claimed in claim 28 capable of recording and reproduction to a laser beam with a wavelength selected from the range of 400 nm to 410 nm and/or 635 nm to 660 nm.

30. The optical recording medium as claimed in claim 10 capable of recording and reproduction to a laser beam with a wavelength selected from the range of 300 nm to 500 nm and/or 500 nm to 700 nm.

31. The optical recording medium as claimed in claim 30 capable of recording and reproduction to a laser beam with a wavelength selected from the range of 400 nm to 500 nm and/or 600 nm to 700 nm.

32. The optical recording medium as claimed in claim 31 capable of recording and reproduction to a laser beam with a wavelength selected from the range of 400 nm to 410 nm and/or 635 nm to 660 nm.

33. A porphycene compound represented by the following formula:

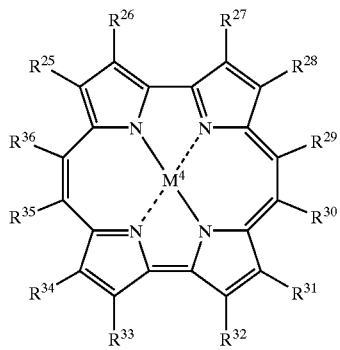

wherein $R^{25}$ to $R^{36}$ independently represent an alkyl or alkoxy group, $M^4$ is a bivalent metal atom.

* * * * *